US012207870B2

(12) United States Patent
Massimini et al.

(10) Patent No.: US 12,207,870 B2
(45) Date of Patent: Jan. 28, 2025

(54) SPECTROSCOPIC TISSUE IDENTIFICATION FOR BALLOON INTRAVASCULAR LITHOTRIPSY GUIDANCE

(71) Applicants: Boston Scientific Scimed, Inc., Maple Grove, MN (US); Bolt Medical, Inc., Carlsbad, CA (US)

(72) Inventors: Daniel Frank Massimini, Brooklyn Park, MN (US); Roger W. McGowan, Otsego, MN (US); Haiping Shao, Plymouth, MN (US); Darrin Dale Beekman, Osseo, MN (US); Christopher A. Cook, Laguna Niguel, CA (US)

(73) Assignees: BOSTON SCIENTIFIC SCIMED, INC., Maple Grove, MN (US); BOLT MEDICAL, INC., Carlsbad, CA (US)

( * ) Notice: Subject to any disclaimer, the term of this patent is extended or adjusted under 35 U.S.C. 154(b) by 129 days.

(21) Appl. No.: 17/343,059

(22) Filed: Jun. 9, 2021

(65) Prior Publication Data

US 2021/0386479 A1 Dec. 16, 2021

Related U.S. Application Data

(60) Provisional application No. 63/039,014, filed on Jun. 15, 2020.

(51) Int. Cl.
*A61B 18/24* (2006.01)
*A61B 5/00* (2006.01)
(Continued)

(52) U.S. Cl.
CPC .......... *A61B 18/245* (2013.01); *A61B 5/0075* (2013.01); *A61B 18/042* (2013.01);
(Continued)

(58) Field of Classification Search
CPC . A61B 18/00; A61B 2017/00; A61B 2018/00; A61F 2/00
See application file for complete search history.

(56) References Cited

U.S. PATENT DOCUMENTS

| 4,649,924 A | 3/1987 | Taccardi |
| 4,699,147 A | 10/1987 | Chilson et al. |

(Continued)

FOREIGN PATENT DOCUMENTS

| AU | 2017205323 | 1/2022 |
| AU | 2019452180 | 1/2022 |

(Continued)

OTHER PUBLICATIONS

International Search Report and Written Opinion, issued by the EP/ISA, in PCT/US2021/048819, dated Jan. 14, 2022.
(Continued)

*Primary Examiner* — Mallika D Fairchild
*Assistant Examiner* — Thien Jason Tran
(74) *Attorney, Agent, or Firm* — Seager, Tufte & Wickhem, LLP

(57) ABSTRACT

A catheter system (100) for placement within a treatment site (106) at a vessel wall (208A) or a heart valve includes an energy source (124), a balloon (104), an energy guide (122A), and a tissue identification system (142). The energy source (124) generates energy. The balloon (104) is positionable substantially adjacent to the treatment site (106). The balloon (104) has a balloon wall (130) that defines a balloon interior (146). The balloon (104) is configured to retain a balloon fluid (132) within the balloon interior (146). The energy guide (122A) is configured to receive energy from the energy source (124) and guide the energy into the balloon interior (146) so that plasma is formed in the balloon fluid (132) within the balloon interior (146). The tissue
(Continued)

identification system (142) is configured to spectroscopically analyze tissue within the treatment site (106). A method for treating a treatment site (106) within or adjacent to a vessel wall (208A) or a heart valve can utilize any of the catheter systems (100) described herein.

31 Claims, 5 Drawing Sheets

(51) Int. Cl.
    *A61B 18/00*     (2006.01)
    *A61B 18/04*     (2006.01)
    *A61B 18/14*     (2006.01)
(52) U.S. Cl.
    CPC .. *A61B 18/1492* (2013.01); *A61B 2018/0022* (2013.01); *A61B 2018/00345* (2013.01)

(56) References Cited

U.S. PATENT DOCUMENTS

| | | |
|---|---|---|
| 4,799,479 A | 1/1989 | Spears |
| 4,913,142 A | 4/1990 | Kittrell et al. |
| 4,932,954 A | 6/1990 | Wondrazek et al. |
| 4,955,895 A | 9/1990 | Sugiyama |
| 4,960,108 A | 10/1990 | Reichel et al. |
| 4,994,059 A | 2/1991 | Kosa et al. |
| 5,034,010 A | 7/1991 | Kittrell et al. |
| 5,041,121 A | 8/1991 | Wondrazek et al. |
| 5,082,343 A | 1/1992 | Coult et al. |
| 5,093,877 A | 3/1992 | Aita et al. |
| 5,104,391 A | 4/1992 | Ingle |
| 5,104,392 A | 4/1992 | Kittrell et al. |
| 5,116,227 A | 5/1992 | Levy |
| 5,152,768 A | 10/1992 | Bhatta |
| 5,173,049 A | 12/1992 | Levy |
| 5,181,921 A | 1/1993 | Makita et al. |
| 5,200,838 A | 4/1993 | Nudelman |
| 5,290,277 A | 3/1994 | Vercimak et al. |
| 5,324,282 A | 6/1994 | Dodick |
| 5,372,138 A | 12/1994 | Crowley |
| 5,387,225 A | 2/1995 | Euteneur |
| 5,400,428 A | 3/1995 | Grace |
| 5,422,926 A | 6/1995 | Smith |
| 5,454,809 A | 10/1995 | Janssen |
| 5,509,917 A | 4/1996 | Cecchetti |
| 5,540,679 A | 7/1996 | Fram |
| 5,562,657 A | 10/1996 | Griffin |
| 5,598,494 A | 1/1997 | Behrmann et al. |
| 5,609,606 A | 3/1997 | O'Boyle |
| 5,611,807 A | 3/1997 | O'Boyle |
| 5,697,377 A | 12/1997 | Wittkamph |
| 5,718,241 A | 2/1998 | Ben-Haim et al. |
| 5,729,583 A | 3/1998 | Tang |
| 5,772,609 A | 6/1998 | Nguyen et al. |
| 5,860,974 A | 1/1999 | Abele |
| 5,891,135 A | 4/1999 | Jackson et al. |
| 5,906,611 A | 5/1999 | Dodick et al. |
| 5,944,697 A | 8/1999 | Benett et al. |
| 6,015,404 A | 1/2000 | Altshuler |
| 6,080,119 A | 6/2000 | Schwarze et al. |
| 6,123,923 A | 9/2000 | Unger |
| 6,139,510 A | 10/2000 | Palermo |
| 6,186,963 B1 | 2/2001 | Schwarze et al. |
| 6,203,537 B1 | 3/2001 | Adrian |
| 6,210,404 B1 | 4/2001 | Shadduck |
| 6,339,470 B1 | 1/2002 | Papademetriou et al. |
| 6,356,575 B1 | 3/2002 | Fukumoto |
| 6,368,318 B1 | 4/2002 | Visuri et al. |
| 6,500,174 B1 | 12/2002 | Maguire et al. |
| 6,514,203 B2 | 2/2003 | Bukshpan |
| 6,514,249 B1 | 2/2003 | Maguire |
| 6,524,251 B2 | 3/2003 | Rabiner et al. |
| 6,538,739 B1 | 3/2003 | Visuri et al. |
| 6,607,502 B1 | 8/2003 | Maguire et al. |
| 6,652,547 B2 | 11/2003 | Rabiner et al. |
| 6,666,834 B2 | 12/2003 | Restle et al. |
| 6,773,447 B2 | 8/2004 | Laguna |
| 6,849,994 B1 | 2/2005 | White et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 7,309,324 B2 | 12/2007 | Hayes et al. |
| 7,470,240 B2 | 12/2008 | Schultheiss et al. |
| 7,539,231 B1 | 5/2009 | Honea et al. |
| 7,569,032 B2 | 8/2009 | Naimark et al. |
| 7,599,588 B2 | 10/2009 | Eberle et al. |
| 7,713,260 B2 | 5/2010 | Lessard |
| 7,758,572 B2 | 7/2010 | Weber et al. |
| 7,810,395 B2 | 10/2010 | Zhou |
| 7,850,685 B2 | 12/2010 | Kunis et al. |
| 7,867,178 B2 | 1/2011 | Simnacher |
| 7,972,299 B2 | 7/2011 | Carter |
| 7,985,189 B1 | 7/2011 | Ogden et al. |
| 8,162,859 B2 | 4/2012 | Schultheiss et al. |
| 8,166,825 B2 | 5/2012 | Zhou |
| 8,192,368 B2 | 6/2012 | Woodruff |
| 8,292,913 B2 | 10/2012 | Warnack |
| 8,328,820 B2 | 12/2012 | Diamant |
| 8,364,235 B2 | 1/2013 | Kordis et al. |
| 8,419,613 B2 | 4/2013 | Saadat |
| 8,439,890 B2 | 5/2013 | Beyar |
| 8,556,813 B2 | 10/2013 | Cashman et al. |
| 8,574,247 B2 | 11/2013 | Adams et al. |
| 8,657,814 B2 | 2/2014 | Werneth |
| 8,709,075 B2 | 4/2014 | Adams et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 8,956,371 B2 | 2/2015 | Hawkins et al. |
| 8,956,374 B2 | 2/2015 | Hawkins et al. |
| 8,986,339 B2 | 3/2015 | Warnack |
| 8,992,817 B2 | 3/2015 | Stamberg |
| 9,005,216 B2 | 4/2015 | Hakala et al. |
| 9,011,462 B2 | 4/2015 | Adams et al. |
| 9,011,463 B2 | 4/2015 | Adams et al. |
| 9,044,618 B2 | 6/2015 | Hawkins et al. |
| 9,044,619 B2 | 6/2015 | Hawkins et al. |
| 9,072,534 B2 | 7/2015 | Adams et al. |
| 9,131,949 B2 | 9/2015 | Coleman et al. |
| 9,138,249 B2 | 9/2015 | Adams et al. |
| 9,138,260 B2 | 9/2015 | Miller et al. |
| 9,180,280 B2 | 11/2015 | Hawkins et al. |
| 9,220,521 B2 | 12/2015 | Hawkins et al. |
| 9,237,984 B2 | 1/2016 | Hawkins et al. |
| 9,289,132 B2 | 3/2016 | Ghaffari et al. |
| 9,289,224 B2 | 3/2016 | Adams et al. |
| 9,320,530 B2 | 4/2016 | Grace |
| 9,333,000 B2 | 5/2016 | Hakala et al. |
| 9,375,223 B2 | 6/2016 | Wallace |
| 9,421,025 B2 | 8/2016 | Hawkins et al. |
| 9,433,428 B2 | 9/2016 | Hakala et al. |
| 9,504,809 B2 | 11/2016 | Bo |
| 9,510,887 B2 | 12/2016 | Burnett |
| 9,522,012 B2 | 12/2016 | Adams |
| 9,554,815 B2 | 1/2017 | Adams et al. |
| 9,555,267 B2 | 1/2017 | Ein-gal |
| 9,566,209 B2 | 2/2017 | Katragadda et al. |
| 9,579,114 B2 | 2/2017 | Mantell et al. |
| 9,629,567 B2 | 4/2017 | Porath et al. |
| 9,642,673 B2 | 5/2017 | Adams |
| 9,662,069 B2 | 5/2017 | De Graff et al. |
| 9,687,166 B2 | 6/2017 | Subramaniam |
| 9,730,715 B2 | 8/2017 | Adams |
| 9,764,142 B2 | 9/2017 | Imran |
| 9,814,476 B2 | 11/2017 | Adams et al. |
| 9,861,377 B2 | 1/2018 | Mantell et al. |
| 9,867,629 B2 | 1/2018 | Hawkins et al. |
| 9,894,756 B2 | 2/2018 | Weinkam et al. |
| 9,955,946 B2 | 5/2018 | Miller et al. |
| 9,974,963 B2 | 5/2018 | Imran |
| 9,974,970 B2 | 5/2018 | Nuta et al. |
| 9,993,292 B2 | 6/2018 | Adams et al. |

(56) References Cited

U.S. PATENT DOCUMENTS

| | | |
|---|---|---|
| 10,039,561 B2 | 8/2018 | Adams et al. |
| 10,136,829 B2 | 11/2018 | Deno et al. |
| 10,149,690 B2 | 12/2018 | Hawkins et al. |
| 10,159,505 B2 | 12/2018 | Hakala et al. |
| 10,194,994 B2 | 2/2019 | Deno et al. |
| 10,201,387 B2 | 2/2019 | Grace et al. |
| 10,206,698 B2 | 2/2019 | Hakala et al. |
| 10,226,265 B2 | 3/2019 | Ku et al. |
| 10,357,264 B2 | 7/2019 | Kat-Kuoy |
| 10,405,923 B2 | 9/2019 | Yu et al. |
| 10,406,031 B2 | 9/2019 | Thyzel |
| 10,420,569 B2 | 9/2019 | Adams |
| 10,441,300 B2 | 10/2019 | Hawkins |
| 10,478,202 B2 | 11/2019 | Adams et al. |
| 10,517,620 B2 | 12/2019 | Adams |
| 10,517,621 B1 | 12/2019 | Hakala et al. |
| 10,537,287 B2 | 1/2020 | Braido et al. |
| 10,555,744 B2 | 2/2020 | Nguyen et al. |
| 10,561,428 B2 | 2/2020 | Eggert et al. |
| 10,646,240 B2 | 5/2020 | Betelia et al. |
| 10,682,178 B2 | 6/2020 | Adams et al. |
| 10,702,293 B2 | 7/2020 | Adams et al. |
| 10,709,462 B2 | 7/2020 | Nguyen et al. |
| 10,758,255 B2 | 9/2020 | Adams |
| 10,842,567 B2 | 11/2020 | Grace et al. |
| 10,959,743 B2 | 3/2021 | Adams et al. |
| 10,966,737 B2 | 4/2021 | Nguyen |
| 10,967,156 B2 | 4/2021 | Gulachenski |
| 10,973,538 B2 | 4/2021 | Hakala et al. |
| 11,000,299 B2 | 5/2021 | Hawkins et al. |
| 11,020,135 B1 | 6/2021 | Hawkins |
| 11,026,707 B2 | 6/2021 | Ku et al. |
| 11,058,492 B2 | 7/2021 | Grace et al. |
| 11,076,874 B2 | 8/2021 | Hakala et al. |
| 11,213,661 B2 | 1/2022 | Spindler |
| 11,229,772 B2 | 1/2022 | Nita |
| 11,229,776 B2 | 1/2022 | Kugler et al. |
| 11,246,659 B2 | 2/2022 | Grace et al. |
| 2001/0016761 A1 | 8/2001 | Rudie |
| 2001/0051784 A1 | 12/2001 | Brisken |
| 2002/0045811 A1 | 4/2002 | Kittrell et al. |
| 2002/0065512 A1 | 5/2002 | Fjield et al. |
| 2002/0082553 A1 | 6/2002 | Duchamp |
| 2002/0183729 A1 | 12/2002 | Farr et al. |
| 2002/0188204 A1 | 12/2002 | McNamara et al. |
| 2003/0009157 A1 | 1/2003 | Levine et al. |
| 2003/0050632 A1 | 3/2003 | Fjield et al. |
| 2003/0065316 A1 | 4/2003 | Levine et al. |
| 2003/0114901 A1 | 6/2003 | Loeb et al. |
| 2003/0125719 A1 | 7/2003 | Furnish |
| 2003/0176873 A1 | 9/2003 | Chernenko et al. |
| 2004/0002677 A1 | 1/2004 | Gentsler |
| 2004/0073251 A1 | 4/2004 | Weber |
| 2004/0097996 A1 | 5/2004 | Rabiner |
| 2004/0133254 A1 | 7/2004 | Sterzer et al. |
| 2004/0162508 A1 | 8/2004 | Uebelacker |
| 2004/0243119 A1 | 12/2004 | Lane et al. |
| 2004/0249401 A1 | 12/2004 | Rabiner |
| 2004/0254570 A1 | 12/2004 | Hadsjicostis |
| 2005/0010095 A1 | 1/2005 | Stewart et al. |
| 2005/0021013 A1 | 1/2005 | Visuri |
| 2005/0080396 A1 | 4/2005 | Rontal |
| 2005/0113722 A1 | 5/2005 | Schultheiss |
| 2005/0171437 A1 | 8/2005 | Carberry |
| 2005/0171527 A1 | 8/2005 | Bhola |
| 2005/0251131 A1 | 11/2005 | Lesh |
| 2005/0259319 A1 | 11/2005 | Brooker |
| 2005/0273014 A1 | 12/2005 | Gianchandani et al. |
| 2005/0277839 A1 | 12/2005 | Alderman et al. |
| 2006/0033241 A1 | 2/2006 | Schewe et al. |
| 2006/0084966 A1 | 4/2006 | Maguire et al. |
| 2006/0098921 A1 | 5/2006 | Benaron et al. |
| 2006/0190022 A1 | 8/2006 | Beyar et al. |
| 2006/0200039 A1 | 9/2006 | Brockway et al. |
| 2006/0221528 A1 | 10/2006 | Li et al. |
| 2006/0241524 A1 | 10/2006 | Lee et al. |
| 2006/0241572 A1 | 10/2006 | Zhou |
| 2006/0241733 A1 | 10/2006 | Zhang et al. |
| 2006/0270976 A1 | 11/2006 | Savage et al. |
| 2007/0043340 A1 | 2/2007 | Thyzel |
| 2007/0060990 A1 | 3/2007 | Satake |
| 2007/0088380 A1 | 4/2007 | Hirszowicz et al. |
| 2007/0118057 A1 | 5/2007 | Ein-gal |
| 2007/0142819 A1 | 6/2007 | El-Nounou et al. |
| 2007/0179496 A1 | 8/2007 | Swoyer |
| 2007/0239082 A1 | 10/2007 | Schultheiss et al. |
| 2007/0255270 A1 | 11/2007 | Carney |
| 2007/0264353 A1 | 11/2007 | Myntti et al. |
| 2007/0270897 A1 | 11/2007 | Skerven |
| 2007/0280311 A1 | 12/2007 | Hofmann |
| 2007/0299392 A1 | 12/2007 | Beyar et al. |
| 2008/0086118 A1 | 4/2008 | Lai |
| 2008/0095714 A1 | 4/2008 | Castella et al. |
| 2008/0097251 A1 | 4/2008 | Babaev |
| 2008/0108867 A1 | 5/2008 | Zhou |
| 2008/0114341 A1 | 5/2008 | Thyzel |
| 2008/0132810 A1 | 6/2008 | Scoseria et al. |
| 2008/0195088 A1 | 8/2008 | Farr et al. |
| 2008/0214891 A1 | 9/2008 | Slenker et al. |
| 2008/0296152 A1 | 12/2008 | Voss |
| 2008/0319356 A1 | 12/2008 | Cain et al. |
| 2009/0036803 A1 | 2/2009 | Warlick et al. |
| 2009/0043300 A1 | 2/2009 | Reitmajer et al. |
| 2009/0054881 A1 | 2/2009 | Krespi |
| 2009/0097806 A1 | 4/2009 | Viellerobe et al. |
| 2009/0125007 A1 | 5/2009 | Splinter |
| 2009/0192495 A1 | 7/2009 | Ostrovsky et al. |
| 2009/0247945 A1 | 10/2009 | Levit |
| 2009/0296751 A1 | 12/2009 | Kewitsch et al. |
| 2009/0299327 A1 | 12/2009 | Tilson et al. |
| 2009/0306533 A1 | 12/2009 | Rousche |
| 2009/0312768 A1 | 12/2009 | Hawkins et al. |
| 2010/0016862 A1 | 1/2010 | Hawkins et al. |
| 2010/0036294 A1 | 2/2010 | Mantell et al. |
| 2010/0114020 A1 | 5/2010 | Hawkins et al. |
| 2010/0114065 A1 | 5/2010 | Hawkins et al. |
| 2010/0125268 A1 | 5/2010 | Gustus et al. |
| 2010/0160903 A1 | 6/2010 | Krespi |
| 2010/0168572 A1 | 7/2010 | Sliwa |
| 2010/0179632 A1 | 7/2010 | Bruszewski et al. |
| 2010/0191089 A1 | 7/2010 | Stebler et al. |
| 2010/0198114 A1 | 8/2010 | Novak et al. |
| 2010/0199773 A1 | 8/2010 | Zhou |
| 2010/0222786 A1 | 9/2010 | Kassab |
| 2010/0234875 A1 | 9/2010 | Allex et al. |
| 2010/0256535 A1 | 10/2010 | Novak et al. |
| 2011/0034832 A1 | 2/2011 | Cioanta et al. |
| 2011/0059415 A1 | 3/2011 | Kasenbacher |
| 2011/0082452 A1 | 4/2011 | Melsky |
| 2011/0082534 A1 | 4/2011 | Wallace |
| 2011/0118634 A1 | 5/2011 | Golan |
| 2011/0144502 A1 | 6/2011 | Zhou et al. |
| 2011/0184244 A1 | 7/2011 | Kagaya et al. |
| 2011/0208185 A1 | 8/2011 | Diamant et al. |
| 2011/0213349 A1 | 9/2011 | Brown |
| 2011/0245740 A1 | 10/2011 | Novak et al. |
| 2011/0257641 A1 | 10/2011 | Hastings et al. |
| 2011/0263921 A1 | 10/2011 | Vrba et al. |
| 2011/0275990 A1 | 11/2011 | Besser et al. |
| 2012/0064141 A1* | 3/2012 | Andreacchi ............ C08J 7/123 427/2.3 |
| 2012/0071715 A1 | 3/2012 | Beyar et al. |
| 2012/0071867 A1 | 3/2012 | Ryan |
| 2012/0071889 A1 | 3/2012 | Mantell et al. |
| 2012/0095335 A1 | 4/2012 | Sverdlik et al. |
| 2012/0095461 A1 | 4/2012 | Herscher et al. |
| 2012/0116289 A1 | 5/2012 | Hawkins et al. |
| 2012/0116486 A1 | 5/2012 | Naga et al. |
| 2012/0123331 A1 | 5/2012 | Satake |
| 2012/0123399 A1 | 5/2012 | Belikov |
| 2012/0157892 A1 | 6/2012 | Reitmajer et al. |
| 2012/0197245 A1 | 8/2012 | Burnett |
| 2012/0203255 A1 | 8/2012 | Hawkins et al. |
| 2012/0221013 A1 | 8/2012 | Hawkins et al. |

(56) References Cited

U.S. PATENT DOCUMENTS

| | | |
|---|---|---|
| 2012/0232409 A1 | 9/2012 | Stahmann |
| 2012/0296367 A1 | 11/2012 | Grovender et al. |
| 2012/0330293 A1 | 12/2012 | Arai |
| 2013/0030431 A1 | 1/2013 | Adams |
| 2013/0030447 A1 | 1/2013 | Adams |
| 2013/0041355 A1 | 2/2013 | Heeren et al. |
| 2013/0046207 A1 | 2/2013 | Capelli |
| 2013/0046293 A1 | 2/2013 | Arai et al. |
| 2013/0053762 A1* | 2/2013 | Rontal ............... A61B 1/015 604/24 |
| 2013/0116714 A1 | 5/2013 | Adams et al. |
| 2013/0190803 A1 | 7/2013 | Angel et al. |
| 2013/0197614 A1 | 8/2013 | Gustus |
| 2013/0218054 A1 | 8/2013 | Sverdlik et al. |
| 2013/0226131 A1 | 8/2013 | Bacino et al. |
| 2013/0253466 A1 | 9/2013 | Campbell |
| 2013/0345617 A1 | 12/2013 | Wallace |
| 2014/0005576 A1 | 1/2014 | Adams |
| 2014/0005706 A1 | 1/2014 | Gelfand et al. |
| 2014/0012186 A1 | 1/2014 | Thyzel |
| 2014/0039002 A1 | 1/2014 | Adams et al. |
| 2014/0039358 A1 | 2/2014 | Zhou et al. |
| 2014/0039513 A1 | 2/2014 | Hakala |
| 2014/0046229 A1 | 2/2014 | Hawkins et al. |
| 2014/0046353 A1 | 2/2014 | Adams |
| 2014/0052146 A1 | 2/2014 | Curtis et al. |
| 2014/0052147 A1 | 2/2014 | Hakala et al. |
| 2014/0058294 A1 | 2/2014 | Gross et al. |
| 2014/0074111 A1 | 3/2014 | Hakala |
| 2014/0114198 A1 | 4/2014 | Samada et al. |
| 2014/0153087 A1 | 6/2014 | Hutchings et al. |
| 2014/0155990 A1 | 6/2014 | Nyuli |
| 2014/0180069 A1 | 6/2014 | Millett |
| 2014/0180126 A1 | 6/2014 | Millett |
| 2014/0180134 A1 | 6/2014 | Hoseit |
| 2014/0188094 A1 | 7/2014 | Islam |
| 2014/0228829 A1 | 8/2014 | Schmitt |
| 2014/0257144 A1 | 9/2014 | Capelli et al. |
| 2014/0257148 A1 | 9/2014 | Jie |
| 2014/0276573 A1 | 9/2014 | Miesel |
| 2014/0288570 A1 | 9/2014 | Adams |
| 2014/0336632 A1 | 11/2014 | Toth |
| 2014/0357997 A1 | 12/2014 | Hartmann |
| 2015/0005576 A1 | 1/2015 | Diodone et al. |
| 2015/0039002 A1 | 2/2015 | Hawkins |
| 2015/0073430 A1 | 3/2015 | Hakala et al. |
| 2015/0080875 A1 | 3/2015 | Kasprzyk et al. |
| 2015/0100048 A1 | 4/2015 | Hiereth et al. |
| 2015/0105715 A1 | 4/2015 | Pikus et al. |
| 2015/0119870 A1 | 4/2015 | Rudie |
| 2015/0141764 A1 | 5/2015 | Harks et al. |
| 2015/0250542 A1 | 9/2015 | Islam |
| 2015/0276689 A1 | 10/2015 | Watanabe et al. |
| 2015/0313732 A1 | 11/2015 | Fulton, III |
| 2015/0359432 A1 | 12/2015 | Ehrenreich |
| 2016/0008016 A1 | 1/2016 | Cioanta et al. |
| 2016/0016016 A1 | 1/2016 | Taylor et al. |
| 2016/0018602 A1 | 1/2016 | Govari et al. |
| 2016/0022294 A1 | 1/2016 | Cioanta et al. |
| 2016/0038087 A1 | 2/2016 | Hunter |
| 2016/0095610 A1 | 4/2016 | Lipowski et al. |
| 2016/0135828 A1 | 5/2016 | Hawkins et al. |
| 2016/0143522 A1 | 5/2016 | Ransbury |
| 2016/0151639 A1 | 6/2016 | Scharf et al. |
| 2016/0183819 A1 | 6/2016 | Burnett |
| 2016/0183957 A1 | 6/2016 | Hakala et al. |
| 2016/0184020 A1* | 6/2016 | Kowalewski ........ A61B 18/24 606/15 |
| 2016/0184022 A1 | 6/2016 | Grace et al. |
| 2016/0184023 A1 | 6/2016 | Grace et al. |
| 2016/0184570 A1 | 6/2016 | Grace et al. |
| 2016/0262784 A1 | 9/2016 | Grace et al. |
| 2016/0270806 A1 | 9/2016 | Wallace |
| 2016/0234534 A1 | 11/2016 | Hawkins et al. |
| 2016/0324564 A1 | 11/2016 | Gerlach et al. |
| 2016/0331389 A1 | 11/2016 | Hakala et al. |
| 2016/0331434 A1* | 11/2016 | Phillips ............... A61B 34/20 |
| 2016/0367274 A1 | 12/2016 | Wallace |
| 2016/0367275 A1 | 12/2016 | Wallace |
| 2017/0049463 A1 | 2/2017 | Popovic et al. |
| 2017/0056035 A1 | 3/2017 | Adams |
| 2017/0056087 A1 | 3/2017 | Buckley |
| 2017/0086867 A1 | 3/2017 | Adams |
| 2017/0119469 A1 | 5/2017 | Shimizu et al. |
| 2017/0119470 A1 | 5/2017 | Diamant et al. |
| 2017/0135709 A1 | 5/2017 | Nguyen et al. |
| 2017/0151421 A1 | 6/2017 | Asher |
| 2017/0209050 A1 | 7/2017 | Fengler et al. |
| 2017/0265942 A1 | 9/2017 | Grace et al. |
| 2017/0303946 A1 | 10/2017 | Ku et al. |
| 2017/0311965 A1 | 11/2017 | Adams |
| 2018/0008348 A1 | 1/2018 | Grace et al. |
| 2018/0042661 A1 | 2/2018 | Long |
| 2018/0042677 A1 | 2/2018 | Yu et al. |
| 2018/0049877 A1 | 2/2018 | Venkatasubramanian |
| 2018/0085174 A1 | 3/2018 | Radtke et al. |
| 2018/0092763 A1 | 4/2018 | Dagan et al. |
| 2018/0095287 A1 | 4/2018 | Jeng et al. |
| 2018/0098779 A1 | 4/2018 | Betelia et al. |
| 2018/0152568 A1 | 6/2018 | Kat-kuoy |
| 2018/0238675 A1 | 8/2018 | Wan |
| 2018/0256250 A1 | 9/2018 | Adams et al. |
| 2018/0280005 A1 | 10/2018 | Parmentier |
| 2018/0303501 A1 | 10/2018 | Hawkins |
| 2018/0303503 A1 | 10/2018 | Eggert et al. |
| 2018/0303504 A1 | 10/2018 | Eggert et al. |
| 2018/0304053 A1 | 10/2018 | Eggert et al. |
| 2018/0333043 A1 | 11/2018 | Teriluc |
| 2018/0360482 A1 | 12/2018 | Nguyen |
| 2019/0029702 A1 | 1/2019 | De Cicco |
| 2019/0029703 A1 | 1/2019 | Wasdyke et al. |
| 2019/0069916 A1 | 3/2019 | Hawkins et al. |
| 2019/0097380 A1 | 3/2019 | Luft et al. |
| 2019/0099588 A1 | 4/2019 | Ramanath et al. |
| 2019/0104933 A1 | 4/2019 | Stern |
| 2019/0117242 A1 | 4/2019 | Lawinger |
| 2019/0150960 A1 | 5/2019 | Nguyen et al. |
| 2019/0175111 A1 | 6/2019 | Genereux et al. |
| 2019/0175300 A1 | 6/2019 | Horn et al. |
| 2019/0175372 A1 | 6/2019 | Boyden et al. |
| 2019/0175407 A1 | 6/2019 | Bacher |
| 2019/0209368 A1 | 7/2019 | Park et al. |
| 2019/0232066 A1 | 8/2019 | Lim et al. |
| 2019/0247680 A1 | 8/2019 | Mayer |
| 2019/0262594 A1 | 8/2019 | Ogata et al. |
| 2019/0265419 A1 | 8/2019 | Tayebati |
| 2019/0282249 A1 | 9/2019 | Tran et al. |
| 2019/0282250 A1 | 9/2019 | Tran et al. |
| 2019/0328259 A1 | 10/2019 | Deno et al. |
| 2019/0365400 A1 | 12/2019 | Adams et al. |
| 2019/0388002 A1 | 12/2019 | Bozsak et al. |
| 2019/0388110 A1 | 12/2019 | Nguyen et al. |
| 2019/0388133 A1 | 12/2019 | Sharma |
| 2019/0388151 A1 | 12/2019 | Bhawalkar |
| 2020/0000484 A1 | 1/2020 | Hawkins |
| 2020/0008856 A1 | 1/2020 | Harmouche |
| 2020/0022754 A1 | 1/2020 | Cottone |
| 2020/0038087 A1 | 2/2020 | Harmouche |
| 2020/0046949 A1 | 2/2020 | Chisena et al. |
| 2020/0054352 A1 | 2/2020 | Brouillette et al. |
| 2020/0061931 A1 | 2/2020 | Brown et al. |
| 2020/0069371 A1 | 3/2020 | Brown et al. |
| 2020/0085458 A1 | 3/2020 | Nguyen et al. |
| 2020/0085459 A1 | 3/2020 | Adams |
| 2020/0107960 A1 | 4/2020 | Bacher |
| 2020/0108236 A1 | 4/2020 | Salazar et al. |
| 2020/0129195 A1 | 4/2020 | McGowan et al. |
| 2020/0129741 A1 | 4/2020 | Kawwas |
| 2020/0155812 A1 | 5/2020 | Zhang et al. |
| 2020/0197019 A1 | 6/2020 | Harper |
| 2020/0205890 A1 | 7/2020 | Harlev |
| 2020/0246032 A1 | 8/2020 | Betelia et al. |
| 2020/0289202 A1 | 9/2020 | Miyagawa et al. |
| 2020/0297366 A1 | 9/2020 | Nguyen et al. |

(56) References Cited

U.S. PATENT DOCUMENTS

| | | |
|---|---|---|
| 2020/0337717 A1 | 10/2020 | Walzman |
| 2020/0383724 A1 | 12/2020 | Adams et al. |
| 2020/0397230 A1 | 12/2020 | Massimini et al. |
| 2020/0397453 A1 | 12/2020 | McGowan et al. |
| 2020/0398033 A1 | 12/2020 | McGowan et al. |
| 2020/0405333 A1 | 12/2020 | Massimini et al. |
| 2020/0405391 A1 | 12/2020 | Massimini et al. |
| 2020/0406009 A1 | 12/2020 | Massimini et al. |
| 2020/0406010 A1 | 12/2020 | Massimini et al. |
| 2021/0038237 A1 | 2/2021 | Adams |
| 2021/0085347 A1 | 3/2021 | Phan et al. |
| 2021/0085348 A1 | 3/2021 | Nguyen |
| 2021/0085383 A1 | 3/2021 | Vo et al. |
| 2021/0128241 A1 | 5/2021 | Schultheis |
| 2021/0137598 A1 | 5/2021 | Cook |
| 2021/0153939 A1 | 5/2021 | Cook |
| 2021/0177445 A1 | 6/2021 | Nguyen |
| 2021/0186613 A1 | 6/2021 | Cook |
| 2021/0212765 A1 | 7/2021 | Verhagen |
| 2021/0220052 A1 | 7/2021 | Cook |
| 2021/0220053 A1 | 7/2021 | Cook |
| 2021/0244473 A1 | 8/2021 | Cook et al. |
| 2021/0267685 A1 | 9/2021 | Schultheis |
| 2021/0275247 A1 | 9/2021 | Schultheis |
| 2021/0275249 A1 | 9/2021 | Massimini et al. |
| 2021/0282792 A1 | 9/2021 | Adams et al. |
| 2021/0290259 A1 | 9/2021 | Hakala et al. |
| 2021/0290286 A1 | 9/2021 | Cook |
| 2021/0290305 A1 | 9/2021 | Cook |
| 2021/0298603 A1 | 9/2021 | Feldman |
| 2021/0307828 A1 | 10/2021 | Schultheis |
| 2021/0330384 A1 | 10/2021 | Cook |
| 2021/0338258 A1 | 11/2021 | Hawkins et al. |
| 2021/0353359 A1 | 11/2021 | Cook |
| 2021/0369348 A1 | 12/2021 | Cook |
| 2021/0378743 A1 | 12/2021 | Massimini et al. |
| 2021/0378744 A1* | 12/2021 | Fanier ............ A61B 17/22012 |
| 2021/0386479 A1 | 12/2021 | Massimini et al. |
| 2022/0000505 A1 | 1/2022 | Hauser |
| 2022/0000506 A1 | 1/2022 | Hauser |
| 2022/0000507 A1 | 1/2022 | Hauser |
| 2022/0000508 A1 | 1/2022 | Schmitt et al. |
| 2022/0000509 A1 | 1/2022 | Laser et al. |
| 2022/0000551 A1 | 1/2022 | Govari et al. |
| 2022/0008130 A1 | 1/2022 | Massimini et al. |
| 2022/0008693 A1 | 1/2022 | Humbert et al. |
| 2022/0015785 A1 | 1/2022 | Hakala et al. |
| 2022/0021190 A1 | 1/2022 | Pecquois |
| 2022/0022902 A1 | 1/2022 | Spano |
| 2022/0022912 A1 | 1/2022 | Efremkin |
| 2022/0023528 A1 | 1/2022 | Long et al. |
| 2022/0071704 A1 | 3/2022 | Le |
| 2022/0168594 A1 | 6/2022 | Mayer |
| 2022/0183738 A1 | 6/2022 | Flores et al. |
| 2022/0218402 A1 | 7/2022 | Schultheis |
| 2022/0249165 A1 | 8/2022 | Cook |
| 2022/0273324 A1 | 9/2022 | Schultheis |
| 2022/0354578 A1 | 11/2022 | Cook |
| 2022/0387106 A1 | 12/2022 | Cook |
| 2023/0013920 A1 | 1/2023 | Massimini |

FOREIGN PATENT DOCUMENTS

| | | |
|---|---|---|
| CA | 2229806 | 3/1997 |
| CA | 2983655 | 10/2016 |
| CN | 102057422 | 5/2011 |
| CN | 109223100 | 1/2019 |
| CN | 110638501 A | 1/2020 |
| CN | 106794043 | 3/2020 |
| CN | 11399346 | 1/2022 |
| CN | 107411805 | 1/2022 |
| CN | 107899126 | 1/2022 |
| CN | 109475378 | 1/2022 |
| CN | 113876388 | 1/2022 |
| CN | 113877044 | 1/2022 |
| CN | 113907838 | 1/2022 |
| CN | 113951972 A | 1/2022 |
| CN | 113951973 A | 1/2022 |
| CN | 113974765 | 1/2022 |
| CN | 113974826 A | 1/2022 |
| CN | 215384399 | 1/2022 |
| CN | 215386905 | 1/2022 |
| CN | 215458400 | 1/2022 |
| CN | 215458401 | 1/2022 |
| CN | 215505065 | 1/2022 |
| CN | 215534803 | 1/2022 |
| CN | 215537694 | 1/2022 |
| CN | 215584286 | 1/2022 |
| CN | 215606068 | 1/2022 |
| CN | 215651393 | 1/2022 |
| CN | 215651394 | 1/2022 |
| CN | 215651484 | 1/2022 |
| CN | 215653328 | 1/2022 |
| DE | 3038445 A1 | 5/1982 |
| DE | 3836337 A1 | 4/1990 |
| DE | 3913027 A1 | 10/1990 |
| DE | 202008016760 | 3/2009 |
| DE | 102007046902 | 4/2009 |
| DE | 102008034702 | 1/2010 |
| DE | 102009007129 | 8/2010 |
| DE | 202010009899 | 11/2010 |
| DE | 102013201928 | 8/2014 |
| DE | 102020117713 | 1/2022 |
| EP | 0119296 | 9/1984 |
| EP | 0261831 B1 | 6/1992 |
| EP | 558297 A2 | 9/1993 |
| EP | 0571306 A1 | 11/1993 |
| EP | 1179993 A1 | 2/2002 |
| EP | 1946712 | 7/2008 |
| EP | 1946712 A1 | 7/2008 |
| EP | 2157569 | 2/2010 |
| EP | 2879595 | 6/2015 |
| EP | 2879595 A1 | 6/2015 |
| EP | 2944264 A1 | 6/2015 |
| EP | 3226795 A1 | 10/2017 |
| EP | 3318204 | 5/2018 |
| EP | 3461438 A1 | 4/2019 |
| EP | 3473195 A1 | 4/2019 |
| EP | 3643260 A1 | 4/2020 |
| EP | 3076881 B1 | 1/2022 |
| EP | 3932342 | 1/2022 |
| EP | 3936140 | 1/2022 |
| EP | 4051154 | 9/2022 |
| GB | 1082397 | 9/1967 |
| JP | S62275446 A | 11/1987 |
| KR | 20050098932 | 10/2005 |
| KR | 20080040111 | 5/2008 |
| KR | 20160090877 A | 8/2016 |
| WO | WO9007904 A1 | 7/1990 |
| WO | WO9105332 A1 | 4/1991 |
| WO | 9203095 A1 | 3/1992 |
| WO | WO9208515 | 5/1992 |
| WO | 9902095 A1 | 1/1999 |
| WO | 1999002095 A1 | 1/1999 |
| WO | 9920189 A1 | 4/1999 |
| WO | 1999020189 A1 | 4/1999 |
| WO | WO200067648 | 11/2000 |
| WO | WO2000067648 A1 | 11/2000 |
| WO | WO0103599 A2 | 1/2001 |
| WO | 20060006169 A2 | 1/2006 |
| WO | WO2006006169 | 1/2006 |
| WO | WO2009121017 | 10/2009 |
| WO | WO2009149321 A1 | 12/2009 |
| WO | WO2009152352 A2 | 12/2009 |
| WO | 2010042653 A1 | 4/2010 |
| WO | WO2011094379 | 8/2011 |
| WO | 20110126580 | 10/2011 |
| WO | WO2011126580 A3 | 10/2011 |
| WO | WO2012025833 | 3/2012 |
| WO | WO20120052924 A1 | 4/2012 |
| WO | WO2012099974 A2 | 7/2012 |
| WO | WO20120120495 A2 | 9/2012 |
| WO | WO2013119662 | 8/2013 |
| WO | 20130169807 A1 | 11/2013 |

(56) References Cited

FOREIGN PATENT DOCUMENTS

| | | |
|---|---|---|
| WO | WO2013169807 | 11/2013 |
| WO | WO2014022436 A1 | 2/2014 |
| WO | WO2014025397 A1 | 2/2014 |
| WO | WO20140022867 A1 | 2/2014 |
| WO | WO2014138582 | 9/2014 |
| WO | WO2015056662 | 4/2015 |
| WO | WO2015097251 A2 | 7/2015 |
| WO | 20150177790 A1 | 11/2015 |
| WO | WO2016089683 A1 | 6/2016 |
| WO | WO2016090175 | 6/2016 |
| WO | WO2016109739 | 7/2016 |
| WO | WO2016151595 A1 | 9/2016 |
| WO | WO2017004432 A1 | 1/2017 |
| WO | WO20170192869 A1 | 11/2017 |
| WO | 20180022641 A1 | 2/2018 |
| WO | WO2018022593 A1 | 2/2018 |
| WO | WO2018083666 | 5/2018 |
| WO | 20180175322 A1 | 9/2018 |
| WO | WO2018175322 | 9/2018 |
| WO | WO2018191013 | 10/2018 |
| WO | WO2019200201 A1 | 10/2019 |
| WO | WO2019215869 A1 | 11/2019 |
| WO | WO2019222843 | 11/2019 |
| WO | WO2020056031 | 3/2020 |
| WO | WO20200086361 A1 | 4/2020 |
| WO | WO2020089876 A1 | 5/2020 |
| WO | WO2020157648 | 8/2020 |
| WO | WO2020256898 | 12/2020 |
| WO | WO2020256898 A1 | 12/2020 |
| WO | WO2020256949 | 12/2020 |
| WO | WO2020256949 A1 | 12/2020 |
| WO | WO2020263469 A1 | 12/2020 |
| WO | WO2020263685 A1 | 12/2020 |
| WO | WO2020263687 A1 | 12/2020 |
| WO | WO2020263688 A1 | 12/2020 |
| WO | WO2020263689 A1 | 12/2020 |
| WO | WO2021061451 | 4/2021 |
| WO | WO2021067563 | 4/2021 |
| WO | WO2021086571 A1 | 5/2021 |
| WO | WO2021096922 A1 | 5/2021 |
| WO | WO2021101766 | 5/2021 |
| WO | WO2021101766 A1 | 5/2021 |
| WO | WO2021126762 | 6/2021 |
| WO | WO2021162855 A1 | 8/2021 |
| WO | WO2021173417 A1 | 9/2021 |
| WO | WO2021183367 A1 | 9/2021 |
| WO | WO2021183401 A1 | 9/2021 |
| WO | WO2021188233 A1 | 9/2021 |
| WO | WO2021202248 A1 | 10/2021 |
| WO | WO2021231178 A1 | 11/2021 |
| WO | WO2021247685 A1 | 12/2021 |
| WO | WO2021257425 A1 | 12/2021 |
| WO | WO2022007490 | 1/2022 |
| WO | WO2022008440 | 1/2022 |
| WO | WO2022010767 A1 | 1/2022 |
| WO | WO2022055784 | 3/2022 |
| WO | WO2022125525 | 6/2022 |
| WO | WO2022154954 | 7/2022 |
| WO | WO2022173719 | 8/2022 |
| WO | WO2022187058 | 9/2022 |
| WO | WO2022216488 | 10/2022 |
| WO | WO2022240674 | 11/2022 |
| WO | WO2022260932 | 12/2022 |

OTHER PUBLICATIONS

International Search Report and Written Opinion, PCT Application Serial No. PCT/US2022/047751 issued Feb. 10, 2023, by the European Patent Office. (56PCT).
International Search Report and Written Opinion dated Aug. 25, 2022 in PCT Application Serial No. PCT US/2022/028035.
International Search Report and Written Opinion dated Sep. 15, 2022 in PCT Application Serial No. PCT US/2022/032045.
International Search Report and Written Opinion dated Jun. 28, 2022, in PCT Application Serial No. PCT/US2022/015577.
International Search Report and Written Opinion dated Jun. 27, 2022, in PCT Application Serial No. PCT/US2022/022460.
Medlight, "Cylindrical light diffuser Model RD-ML", Medlight S.A., Switzerland. 2015. (This reference was cited in a prior Information Disclosure Statement. However, the relevant date was missing. The date has now been added.).
Medlight, "Cylindircal light diffuser Model RD", Medlight S.A., Switzerland. 2015. (This reference was cited in a prior Information Disclosure Statement. However, the relevant date was missing. The date has now been added.).
Ohl, Siew-Wan, et al. "Bubbles with shock waves and ultrasound: a review", Interface Focus, pp. 1-15, vol. 5, The Royal Society Publishing. Oct. 2015. (This reference was cited in a prior Information Disclosure Statement. However, the relevant date was missing. The date has now been added.).
Schafter+Kirchhoff, Laser Beam Couplers series 60SMS for coupling into single-mode and polarization-maintaining fiber cables, Schafter+Kirchhoff, pp. 1-5, Germany. Dec. 2, 2021. (This reference was cited in a prior Information Disclosure Statement. However, the relevant date was missing. The date has now been added.).
Meng et al., "Accurate Recovery of Atrial Endocardial Potential Maps From Non-contact Electrode Data." Auckland Bioengineering Institute. (ID 1421). May 2019. (This reference was cited in a prior Information Disclosure Statement. However, the relevant date was missing. The date has now been added.).
Jiang et al., "Multielectrode Catheter for Substrate Mapping for Scar-related VT Ablation: A Comparison Between Grid Versus Linear Configurations." UChicago Medicine, Center for Arrhythmia Care, Chicago IL (ID 1368). Poster for conference in San Francisco, May 8-11, 2019. (This reference was cited in a prior Information Disclosure Statement. However, the relevant date was missing. The date has now been added.).
Sacher et al., "Comparison of Manual Vs Automatic Annotation to Identify Abnormal Substrate for Scar Related VT Ablation." LIRYC Institute, Bordeaux University Hospital, France (ID 1336). Poster for conference in San Francisco, May 8-11, 2019. (This reference was cited in a prior Information Disclosure Statement. However, the relevant date was missing. The date has now been added.).
International Search Report and Written Opinion dated Aug. 20, 2021 in PCT Application Serial No. PCT/US2021/031130.
International Search Report and Written Opinion, issued by the European Patent Office for PCT/2021/XXX, dated Sep. 30, 2021.
International Search Report and Written Opinion dated Nov. 8, 2022 in PCT Application Serial No. PCT US/2022/039678.
International Search Report and Written Opinion dated Apr. 4, 2022 in PCT Application Serial No. PCT/US2021/062170.
International Search Report and Written Opinion dated Apr. 4, 2022 in PCT Application Serial No. PCT/US2021/065073.
Partial Search Report and Provisional Opinion dated May 3, 2022 in PCT Application No. PCT/ US2022/015577.
International Search Report and Written Opinion dated May 13, 2022 in PCT Application Serial No. PCT/US2022/017562.
AccuCoat, "Beamsplitter: Divide, combine & conquer"; 2023.
Lin et al., "Photoacoustic imaging", Science Direct; 2021.
Zhou et al., "Photoacoustic Imaging with fiber optic technology: A review", Science Direct; 2020.
International Search Report and Written Opinion issued by the European Patent Office, for Serial No. PCT/US2022/053775, dated Apr. 21, 2023. (Re 45PCT).
International Search Report and Written Opinion issued by the European Patent Office, for Serial No. PCT/US2023/011497, dated Apr. 28, 2023. (Re 54PCT).
International Search Report and Written Opinion issued by the European Patent Office, for Serial No. PCT/US2023/012599, dated May 19, 2023. (Re 57PCT).
PathFinder Digital, "Free Space Optics vs. Fiber Optics", 2023.
International Search Report and Written Opinion, issued in Application Serial No. PCT/US2023/016152, dated Jul. 12, 2023.
Davletshin, Yevgeniy R., "A Computational Analysis of Nanoparticle-Mediated Optical Breakdown", A dissertation presented to Ryerson

(56) References Cited

OTHER PUBLICATIONS

University in Partial Fulfillment of the requirements for the degree of Doctor of Philosophy in the Program of Physics, Toronto, Ontario, CA 2017.

Vogel, A., et al. "Acoustic transient generation by laser-produced cavitation bubbles near solid boundaries", Journal Acoustical Society of America, 1988, pp. 719-731, vol. 84.

Asshauer, T., et al. "Acoustic transient generation by holmium-laser-induced cavitation bubbles", Journal of Applied Physics, Nov. 1, 1994, pp. 5007-5013, vol. 76, No. 9, American Institute of Physics.

Zheng, W., "Optic Lenses Manufactured on Fiber Ends", 2015, Splicer Engineering AFL, Duncan, SC USA.

Ali, Ziad A., et al. "Optical Coherence Tomography Characterization of Coronary Lithoplasty for Treatment of Calcified Lesions", JACC: Cardiovascular Imaging, 2017, pp. 897-906, vol. 109, No. 8, Elsevier.

Ali, Ziad A., et al. "Intravascular lithotripsy for treatment of stent underexpansion secondary to severe coronary calcification" 2018, European Society of Cardiology.

Ashok, Praveen C., et al. "Raman spectroscopy bio-sensor for tissue discrimination in surgical robotics—full article", Journal of Biophotonics, 2014, pp. 103-109, vol. 7, No. 1-2.

Ashok, Praveen C., et al. "Raman spectroscopy bio-sensor for tissue discrimination in surgical robotics—proof" Journal of Biophotonics 7, 2014, No. 1-2.

Bian, D. C., et al. "Experimental Study of Pulsed Discharge Underwater Shock-Related Properties in Pressurized Liquid Water", Hindawi Advances in Materials Science and Engineering, Jan. 2018, 12 pages, vol. 2018, Article ID 8025708.

Bian, D. C., et al. "Study on Breakdown Delay Characteristics Based on High-voltage Pulse Discharge in Water with Hydrostatic Pressure", Journal of Power Technologies 97(2), 2017, pp. 89-102.

Doukas, A. G., et al. "Biological effects of laser induced shock waves: Structural and functional cell damage in vitro", Ultrasound in Medicine and Biology, 1993, pp. 137-146, vol. 19, Issue 2, Pergamon Press, USA.

Brodmann, Marianne et al. "Safety and Performance of Lithoplasty for Treatment of Calcified Peripheral Artery Lesions", JACC, 2017, vol. 70, No. 7.

Brouillette, M., "Shock Waves at Microscales", 2003, pp. 3-12, Springer-Verlag.

Mirshekari, G., et al. "Shock Waves in Microchannels", 2013, pp. 259-283, vol. 724, Cambridge University Press.

"Bubble Dynamics and Shock Waves", Springer, 2013, Springer-Verlag, Berlin Heildelberg.

Hardy, Luke A., et al. "Cavitation Bubble Dynamics During Thulium Fiber Laser Lithotripsy", SPIE, Feb. 29, 2016, vol. 9689, San Francisco, California, USA.

Claverie, A., et al. "Experimental characterization of plasma formation and shockwave propagation induced by high power pulsed underwater electrical discharge", Review of Scientific Instruments, 2014, American Institute of Physics.

Blackmon, Richard L., et al. "Comparison of holmium: YAG and thulium fiber laser lithotripsy ablation thresholds, ablation rates, and retropulsion effects", Journal of Biomedical Optics, 2011, vol. 16(7), SPIE.

Debasis, P., et al. "Continuous-wave and quasi-continuous wave thulium-doped all-fiber laser: implementation on kidney stone fragmentations", Applied Optics, Aug. 10, 2016, vol. 55, No. 23, Optical Society of America.

Cook, Jason R., et al. "Tissue mimicking phantoms for photoacoustic and ultrasonic imaging", Biomedical Optics Express, 2011, vol. 2, No. 11, Optical Society of America.

Deckelbaum, Lawrence I., "Coronary Laser Angioplasty", Lasers in Surgery and Medicine, 1994, pp. 101-110, Wiley-Liss Inc.

Costanzo, F., "Underwater Explosion Phenomena and Shock Physics", Research Gate, 2011.

Mizeret, J. C., et al. "Cylindrical fiber optic light diffuser for medical applications", Lasers in Surgery and Medicine, 1996, pp. 159-167, vol. 19, Issue 2, Wiley-Liss Inc., Lausanne, Switzerland.

De Silva, K., et al. "A Calcific, Undilatable Stenosis Lithoplasty, a New Tool in the Box?", JACC: Cardiovascular Interventions, 2017, vol. 10, No. 3, Elsevier.

Vesselov, L., et al. "Design and performance of thin cylindrical diffusers created in Ge-doped multimode optical fibers", Applied Optics, 2005, pp. 2754-2758, vol. 44, Issue 14, Optical Society of America.

Hutchens, Thomas C., et al. "Detachable fiber optic tips for use in thulium fiber laser lithotripsy", Journal of Biomedical Optics, Mar. 2013, vol. 18(3), SPIE.

Kostanski, Kris L., et al. "Development of Novel Tunable Light Scattering Coating Materials for Fiber Optic Diffusers in Photodynamic Cancer Therapy", Journal of Applied Polymer Science, 2009, pp. 1516-1523, vol. 112, Wiley InterScience.

Kristiansen, M., et al. "High Voltage Water Breakdown Studies", DoD, 1998, Alexandria, VA, USA.

Dwyer, J. R., et al. "A study of X-ray emission from laboratory sparks in air at atmospheric pressure", Journal of Geophysical Research, 2008, vol. 113, American Geophysical Union.

Jansen, Duco E., et al. "Effect of Pulse Duration on Bubble Formation and Laser-Induced Pressure Waves During Holmium Laser Ablation", Lasers in Surgery and Medicine 18, 1996, pp. 278-293, Wiley-Liss Inc., Austin, TX, USA.

Shangguan, HanQun et al. "Effects of Material Properties on Laser-induced Bubble Formation in Absorbing Liquids and on Submerged Targets", SPIE, 1997, pp. 783-791, vol. 2869.

Varghese, B., et al. "Effects of polarization and absorption on laser induced optical breakdown threshold for skin rejuvenation", SPIE, Mar. 9, 2016, vol. 9740, SPIE, San Francisco, USA.

Varghese, B., et al. "Effects of polarization and apodization on laser induced optical breakdown threshold", Optics Express, Jul. 29, 2013, vol. 21, No. 15, Optical Society of America.

Bonito, Valentina, "Effects of polarization, plasma and thermal initiation pathway on irradiance threshold of laser induced optical breakdown", Philips Research, 2013, The Netherlands.

Vogel, A. et al. "Energy balance of optical breakdown in water at nanosecond to femtosecond time scales", Applied Physics B 68, 1999, pp. 271-280, Springer-Verlag.

Kang, Hyun W., et al. "Enhanced photocoagulation with catheter based diffusing optical device", Journal of Biomedical Optics, Nov. 2012, vol. 17(11), SPIE.

Esch, E., et al. "A Simple Method for Fabricating Artificial Kidney Stones of Different Physical Properties", National Institute of Health Public Access Author Manuscript, Aug. 2010.

Isner, Jeffrey M., et al. "Excimer Laser Atherectomy", Circulation, Jun. 1990, vol. 81, No. 6, American Heart Association, Dallas, TX, USA.

Israel, Douglas H., et al. "Excimer Laser-Facilitated Balloon Angioplasty of a Nondilateable Lesion", JACC, Oct. 1991, vol. 18, No. 4, American College of Cardiology, New York, USA.

Van Leeuwen, Ton G., et al. "Excimer Laser Induced Bubble: Dimensions, Theory, and Implications for Laser Angioplasty", Lasers in Surgery and Medicine 18, 1996, pp. 381-390, Wiley-Liss Inc., Utrecht, The Netherlands.

Nguyen, H., et al. "Fabrication of multipoint side-firing optical fiber by laser micro-ablation", Optics Letters, May 1, 2017, vol. 42, No. 9, Optical Society of America.

Zheng, W., "Optic Lenses Manufactured on Fiber Ends", 2015, IEEE, Duncan, SC, USA.

Whitesides, George M., et al. "Fluidic Optics", 2006, vol. 6329, SPIE, Cambridge, MA, USA.

Forero, M., et al. "Coronary lithoplasty: a novel treatment for stent underexpansion", Cardiovascular Flashlight, 2018, European Society of Cardiology.

Ghanate, A. D., et al. "Comparative evaluation of spectroscopic models using different multivariate statistical tools in a multicancer scenario", Journal of Biomedical Optics, Feb. 2011, pp. 1-9, vol. 16(2), SPIE.

(56) References Cited

OTHER PUBLICATIONS

Roberts, Randy M., et al. "The Energy Partition of Underwater Sparks", The Journal of the Acoustical Society of America, Jun. 1996, pp. 3465-3474, Acoustical Society of America, Austin, TX, USA.
Blackmon, Richard L., et al. "Holmium: YAG Versus Thulium Fiber Laser Lithotripsy", Lasers in Surgery and Medicine, 2010, pp. 232-236, Wiley-Liss Inc.
Varghese, B., "Influence of absorption induced thermal initiation pathway on irradiance threshold for laser induced breakdown", Biomedical Optics Express, 2015, vol. 6, No. 4, Optical Society of America.
Noack, J., "Influence of pulse duration on mechanical effects after laser-induced breakdown in water", Journal of Applied Physics, 1998, pp. 7488-EOA, vol. 83, American Institute of Physics.
Van Leeuwen, Ton G., et al. "Intraluminal Vapor Bubble Induced by Excimer Laser Pulse Causes Microsecond Arterial Dilation and Invagination Leading to Extensive Wall Damage in the Rabbit", Circulation, Apr. 1993, vol. 87, No. 4, American Heart Association, Dallas, TX, USA.
Stelzle, F., et al. "Diffuse Reflectance Spectroscopy for Optical Soft Tissue Differentiation as Remote Feedback Control for Tissue-Specific Laser Surgery", Lasers in Surgery and Medicine, 2010, pp. 319-325, vol. 42, Wiley-Liss Inc.
Stelzle, F., et al. Tissue Discrimination by Uncorrected Autofluorescence Spectra: A Proof-of-Principle Study for Tissue-Specific Laser Surgery, Sensors, 2013, pp. 13717-13731, vol. 13, Basel, Switzerland.
Tagawa, Y., et al. "Structure of laser-induced shock wave in water", Japan Society for the Promotion of Science, 2016.
Shen, Y., et al. "Theoretical and experimental studies of directivity of sound field generated by pulsed laser induced breakdown in liquid water", SPIE, 2013, pp. 8796141-8796148, vol. 8796, SPIE.
Preisack, M., et al. "Ultrafast imaging of tissue ablation by a XeCl excimer laser in saline", Lasers in Surgery and Medicine, 1992, pp. 520-527, vol. 12, Wiley-Liss Inc.
Versluis, M., et al. "How Snapping Shrimp Snap: Through Cavitating Bubbles", Science Mag, 2000, pp. 2114-2117, vol. 289, American Association for the Advancement of Science, Washington DC, USA.
Yan, D., et al. "Study of the Electrical Characteristics, Shock-Wave Pressure Characteristics, and Attenuation Law Based on Pulse Discharge in Water", Shock and Vibration, 2016, pp. 1-11, vol. 2016, Article ID 6412309, Hindawi Publishing Corporation.
Zhang, Q., et al. "Improved Instruments and Methods for the Photographic Study of Spark-Induced Cavitation Bubbles", Water, 2018, pp. 1-12, vol. 10, No. 1683.
"Damage threshold of fiber facets", NKT Photonics, 2012, pp. 1-4, Denmark.
Smith, A., et al. "Bulk and surface laser damage of silica by picosecond and nanosecond pulses at 1064 nm", Applied Optics, 2008, pp. 4812-4832, vol. 47, No. 26, Optical Society of America.
Smith, A., et al. "Deterministic Nanosecond Laser-Induced Breakdown Thresholds in Pure and Yb3 Doped Fused Silica", SPIE, 2007, pp. 6453171-64531712, vol. 6453, SPIE.
Sun, X., et al. "Laser Induced Damage to Large Core Optical Fiber by High Peak Power Laser", Specialty Photonics Division, 2010.
Smith, A., et al. "Nanosecond laser-induced breakdown in pure and Yb3 doped fused silica", SPIE, 2007, vol. 6403, SPIE.
Smith, A., et al. "Optical Damage Limits to Pulse Energy From Fibers", IEEE Journal of Selected Topics in Quantum Electronics, 2009, pp. 153-158, vol. 15, No. 1, IEEE.
Reichel, E., et al. "A Special Irrigation Liquid to Increase the Reliability of Laser-Induced Shockwave Lithotripsy", Lasers in Surgery and Medicine, 1992, pp. 204-209, vol. 12, Wiley-Liss Inc., Graz, Austria.
Reichel, E., et al. "Bifunctional irrigation liquid as an ideal energy converter for laser lithotripsy with nanosecond laser pulses", SPIE Lasers in Urology, Laparoscopy, and General Surgery, 1991, pp. 129-133, vol. 1421, SPIE.
Reichel, E., et al. "Laser-induced Shock Wave Lithotripsy with a Regenerative Energy Converter", Lasers in Medical Science, 1992, pp. 423-425, vol. 7, Bailliere Tindall.
Hardy, L., et al. "Cavitation Bubble Dynamics during Thulium Fiber Laser Lithotripsy", SPIE BiOS, 2016, vol. 9689, SPIE.
Deckelbaum, L., "Coronary Laser Angioplasty", Lasers in Surgery and Medicine, 1994, pp. 101-110, vol. 14, Wiley-Liss Inc., Conneticuit, USA.
Shangguan, H., et al. "Effects of Material Properties on Laser-induced Bubble Formation in Absorbing Liquids and on Submerged Targets", Diagnostic and Therapeutic Cardiovascular Interventions VII, SPIE, 1997, pp. 783-791, vol. 2869, SPIE.
Van Leeuwen, T., et al. "Excimer Laser Induced Bubble: Dimensions, Theory, and Implications for Laser Angioplasty", Lasers in Surgery and Medicine, 1996, pp. 381-390, vol. 18, Wiley-Liss Inc., The Netherlands.
Vogel, A., et al. "Minimization of Cavitation Effects in Pulsed Laser Ablation Illustrated on Laser Angioplasty", Applied Physics, 1996, pp. 173-182, vol. 62, Springer-Verlag.
Vogel, A., et al. "Shock Wave Emission and Cavitation Bubble Generation by Picosecond and Nanosecond Optical Breakdown in Water", The Journal of Acoustical Society of America, 1996, pp. 148-165, vol. 100, No. 1, The Acoustical Society of America.
Varghese, B., et al. "Influence of absorption induced thermal initiation pathway on irradiance threshold for laser induced breakdown", Biomedical Optics Express, 2015, vol. 6, No. 4, Optical Society of America.
Linz, N., et al. "Wavelength dependence of nanosecond infrared laser-induced breakdown in water: Evidence for multiphoton initiation via an intermediate state", Physical Review, 2015, pp. 134114.1-1341141.10, vol. 91, American Physical Society.
International Search Report and Written Opinion dated Jun. 27, 2018, in PCT Application Serial No. PCT/US2018/027121.
International Search Report and Written Opinion dated Jul. 20, 2018, in PCT Application Serial No. PCT/US2018/027801.
International Search Report and Written Opinion dated Jul. 20, 2018, in PCT Application Serial No. PCT/US2018/027784.
European Search Report, for European Patent Application No. 18185152, mailed Dec. 13, 2018.
International Search Report and Written Opinion dated May 22, 2019, in PCT Application Serial No. PCT/US2019/022009.
International Search Report and Written Opinion dated May 29, 2019, in PCT Application Serial No. PCT/US2019/022016.
International Search Report and Written Opinion dated Jun. 22, 2018, in Application Serial No. NL2019807, issued by the European Patent Office.
Noimark, Sacha, et al., "Carbon-Nanotube-PDMS Composite Coatings on Optical Fibers for All-Optical Ultrasound Imaging", Advanced Functional Materials, 2016, pp. 8390-8396, vol. 26, Wiley-Liss Inc.
Chen, Sung-Liang, "Review of Laser-Generated Ultrasound Transmitters and their Applications to All-Optical Ultrasound Transducers and Imaging", Appl. Sci. 2017, 7, 25.
Colchester, R., et al. "Laser-Generated ultrasound with optica fibres using functionalised carbon nanotube composite coatings", Appl. Phys. Lett., 2014, vol. 104, 173504, American Institute of Physics.
Poduval, R., et al. "Optical fiber ultrasound transmitter with electrospun carbon nanotube-polymer composite", Appl. Phys. Lett., 2017, vol. 110, 223701, American Institute of Physics.
Tian, J., et al. "Distributed fiber-optic laser-ultrasound generation based on ghost-mode of tilted fiber Bragg gratings", Optics Express, Mar. 2013, pp. 6109-6114, vol. 21, No. 5, Optical Society of America.
Kim, J., et al. "Optical Fiber Laser-Generated-Focused-Ultrasound Transducers for Intravascular Therapies", IEEE, 2017.
Kang, H., et al. "Enhanced photocoagulation with catheter-based diffusing optical device", Journal of Biomedical Optics, 2012, vol. 17, Issue 11, 118001, SPIE.
International Search Report and Written Opinion dated Jan. 3, 2020, in PCT Application Serial No. PCT/US2019/056579.
Communication Pursuant to Article 94(3) EPC, for European Patent Application No. 18185152.8, mailed Jan. 16, 2019.
European Search Report, for European Patent Application No. 18185152.8, mailed Dec. 20, 2018.

(56) References Cited

OTHER PUBLICATIONS

International Search Report and Written Opinion dated Jul. 29, 2020 in PCT Application Serial No. PCT/US2020/034005.
International Search Report and Written Opinion dated Sep. 11, 2020 in PCT Application Serial No. PCT/US2020/038517.
International Search Report and Written Opinion dated Sep. 9, 2020 in PCT Application Serial No. PCT/US2020/038530.
International Search Report and Written Opinion dated Sep. 11, 2020 in PCT Application Serial No. PCT/US2020/038521.
International Search Report and Written Opinion dated Sep. 7, 2020 in PCT Application Serial No. PCT/US2020/034642.
Vogel, A., et al. "Intraocular Photodisruption With Picosecond and Nanosecond Laser Pulses: Tissue Effects in Cornea, Lens, and Retina", Investigative Ophthalmology & Visual Science, Jun. 1994, pp. 3032-3044, vol. 35, No. 7, Association for Research in Vision and Ophthalmology.
Jones, H. M., et al. "Pulsed dielectric breakdown of pressurized water and salt solutions", Journal of Applied Physics, Jun. 1998, pp. 795-805, vol. 77, No. 2, American Institute of Physics.
Kozulin, I., et al. "The dynamic of the water explosive vaporization on the flat microheater", Journal of Physics: Conference Series, 2018, pp. 1-4, IOP Publishing, Russia.
Cross, F., "Laser Angioplasty", Vascular Medicine Review, 1992, pp. 21-30, Edward Arnold.
Doukas, A. G., et al. "Laser-generated stress waves and their effects on the cell membrane", IEEE Journal of Selected Topics in Quantum Electronics, 1999, pp. 997-1003, vol. 5, Issue 4, IEEE.
Noack, J., et al. "Laser-Induced Plasma Formation in Water at Nanosecond to Femtosecond Time Scales: Calculation of Thresholds, Absorption Coefficients, and Energy Density", IEEE Journal of Quantum Electronics, 1999, pp. 1156-1167, vol. 35, No. 8, IEEE.
Pratsos, A., "The use of Laser for the treatment of coronary artery disease", Bryn Mawr Hospital, 2010.
Li, Xian-Dong, et al. "Influence of deposited energy on shock wave induced by underwater pulsed current discharge", Physics of Plasmas, 2016, vol. 23, American Institute of Physics.
Logunov, S., et al. "Light diffusing optical fiber illumination", Renewable Energy and the Environment Congress, 2013, Corning, NY, USA.
Maxwell, A. D., et al. "Cavitation clouds created by shock scattering from bubbles during histotripsy", Acoustical Society of America, 2011, pp. 1888-1898, vol. 130, No. 4, Acoustical Society of America.
McAteer, James A., et al. "Ultracal-30 Gypsum Artificial Stones for Research on the Mechinisms of Stone Breakage in Shock Wave Lithotripsy", 2005, pp. 429-434, Springer-Verlag.
Vogel, A., et al. "Mechanisms of Intraocular Photodisruption With Picosecond and Nanosecond Laser Pulses", Lasers in Surgery and Medicine, 1994, pp. 32-43, vol. 15, Wiley-Liss Inc., Lubeck, Germany.
Vogel, A., et al. "Mechanisms of Pulsed Laser Ablation of Biological Tissues", Chemical Reviews, 2003, pp. 577-644, vol. 103, No. 2, American Chemical Society.
Medlight, "Cylindrical light diffuser Model RD-ML", Medlight S.A., Switzerland.
Medlight, "Cylindircal light diffuser Model RD", Medlight S.A., Switzerland.
Mayo, Michael E., "Interaction of Laser Radiation with Urinary Calculi", Cranfield University Defense and Security, PhD Thesis, 2009, Cranfield University.
Mirshekari, G., et al. "Microscale Shock Tube", Journal of Microelectromechanical Systems, 2012, pp. 739-747, vol. 21, No. 3, IEEE.
"Polymicro Sculpted Silica Fiber Tips", Molex, 2013, Molex.
Zhou, J., et al. "Optical Fiber Tips and Their Applications", Polymicro Technologies a Subsidiary of Molex, Nov. 2007.
Liang, Xiao-Xuan, et al. "Multi-Rate-Equation modeling of the energy spectrum of laser-induced conduction band electrons in water", Optics Express, 2019, vol. 27, No. 4, Optical Society of America.
Nachabe, R., et al. "Diagnosis of breast cancer using diffuse optical spectroscopy from 500 to 1600 nm: comparison of classification methods", Journal of Biomedical Optics, 2011, vol. 16(8), SPIE.
Naugol'nykh, K. A., et al. "Spark Discharges in Water", Academy of Sciences USSR Institute of Acoustics, 1971, Nauka Publishing Co., Moscow, USSR.
Van Leeuwen, Ton G., et al. "Noncontact Tissue Ablation by Holmium: YSGG Laser Pulses in Blood", Lasers in Surgery and Medicine, 1991, vol. 11, pp. 26-34, Wiley-Liss Inc.
Nyame, Yaw A., et al. "Kidney Stone Models for In Vitro Lithotripsy Research: A Comprehensive Review", Journal of Endourology, Oct. 2015, pp. 1106-1109, vol. 29, No. 10, Mary Ann Liebert Inc., Cleveland, USA.
Ohl, Siew-Wan, et al. "Bubbles with shock waves and ultrasound: a review", Interface Focus, pp. 1-15, vol. 5, The Royal Society Publishing.
Zheng, W., "Optical Lenses Manufactured on Fiber Ends", IEEE, 2015, Splicer Engineering, Duncan SC USA.
Dwyer, P. J., et al. "Optically integrating balloon device for photodynamic therapy", Lasers in Surgery and Medicine, 2000, pp. 58-66, vol. 26, Issue 1, Wiley-Liss Inc., Boston MA USA.
"The New Optiguide DCYL700 Fiber Optic Diffuser Series", Optiguide Fiber Optic Spec Sheet, Pinnacle Biologics, 2014, Pinnacle Biologics, Illinois, USA.
Van Leeuwen, Ton G., et al. "Origin of arterial wall dissections induced by pulsed excimer and mid-infared laser ablation in the pig", JACC, 1992, pp. 1610-1618, vol. 19, No. 7, American College of Cardiology.
Oshita, D., et al. "Characteristic of Cavitation Bubbles and Shock Waves Generated by Pulsed Electric Discharges with Different Voltages", IEEE, 2012, pp. 102-105, Kumamoto, Japan.
Karsch, Karl R., et al. "Percutaneous Coronary Excimer Laser Angioplasty in Patients With Stable and Unstable Angina Pectoris", Circulation, 1990, pp. 1849-1859, vol. 81, No. 6, American Heart Association, Dallas TX, USA.
Murray, A., et al. "Peripheral laser angioplasty with pulsed dye laser and ball tipped optical fibres", The Lancet, 1989, pp. 1471-1474, vol. 2, Issue 8678-8679.
Mohammadzadeh, M., et al. "Photoacoustic Shock Wave Emission and Cavitation from Structured Optical Fiber Tips", Applied Physics Letters, 2016, vol. 108, American Institute of Physics Publishing LLC.
Doukas, A. G., et al. "Physical characteristics and biological effects of laser-induced stress waves", Ultrasound in Medicine and Biology, 1996, pp. 151-164, vol. 22, Issue 2, World Federation for Ultrasound in Medicine and Biology, USA.
Doukas, A. G., et al. "Physical factors involved in stress-wave-induced cell injury: the effect of stress gradient", Ultrasound in Medicine and Biology, 1995, pp. 961-967, vol. 21, Issue 7, Elsevier Science Ltd., USA.
Piedrahita, Francisco S., "Experimental Research Work on a Sub-Millimeter Spark-Gap for Sub Nanosecond Gas Breakdown", Thesis for Universidad Nacional De Colombia, 2012, Bogota, Colombia.
Vogel, A., et al. "Plasma Formation in Water by Picosecond and Nanosecond Nd: YAG Laser Pulses—Part I: Optical Breakdown at Threshold and Superthreshold Irradiance", IEEE Journal of Selected Topics in Quantum Electronics, 1996, pp. 847-859, vol. 2, No. 4, IEEE.
Park, Hee K., et al. "Pressure Generation and Measurement in the Rapid Vaporization of Water on a Pulsed-Laser-Heated Surface", Journal of Applied Physics, 1996, pp. 4072-4081, vol. 80, No. 7, American Institute of Physics.
Cummings, Joseph P., et al. "Q-Switched laser ablation of tissue: plume dynamics and the effect of tissue mechanical properties", SPIE, Laser-Tissue Interaction III, 1992, pp. 242-253, vol. 1646.
Lee, Seung H., et al. "Radial-firing optical fiber tip containing conical-shaped air-pocket for biomedical applications", Optics Express, 2015, vol. 23, No. 16, Optical Society of America.
Hui, C., et al. "Research on sound fields generated by laser-induced liquid breakdown", Optica Applicata, 2010, pp. 898-907, vol. XL, No. 4, Xi'an, China.

(56) References Cited

OTHER PUBLICATIONS

Riel, Louis-Philippe, et al. "Characterization of Calcified Plaques Retrieved From Occluded Arteries and Comparison with Potential Artificial Analogues", Proceedings of the ASME 2014 International Mechanical Engineering Congress and Exposition, 2014, pp. 1-11, ASME, Canada.
Roberts, Randy M., et al. "The Energy Partition of Underwater Sparks", The Journal of the Acoustical Society of America, 1996, pp. 3465-3475, vol. 99, No. 6, Acoustical Society of America.
Rocha, R., et al. "Fluorescence and Reflectance Spectroscopy for Identification of Atherosclerosis in Human Carotid Arteries Using Principal Components Analysis", Photomedicine and Lsser Surgery, 2008, pp. 329-335, vol. 26, No. 4, Mary Ann Liebert Inc.
Scepanovic, Obrad R., et al. "Multimodal spectroscopy detects features of vulnerable atherosclerotic plaque", Journal of Biomedical Optics, 2011, pp. 1-10, vol. 16, No. 1, SPIE.
Serruys, P. W., et al. "Shaking and Breaking Calcified Plaque Lithoplasty, a Breakthrough in Interventional Armamentarium?", JACC: Cardiovascular Imaging, 2017, pp. 907-911, vol. 10, No. 8, Elsevier.
Vogel, A., et al. "Shock wave emission and cavitation bubble generation by picosecond and nanosecond optical breakdown in water", The Journal of the Acoustical Society of America, 1996, pp. 148-165, vol. 100, No. 1, Acoustical Society of America.
Vogel, A., et al. "Shock-Wave Energy and Acoustic Energy Dissipation After Laser-induced Breakdown", SPIE, 1998, pp. 180-189, vol. 3254, SPIE.
International Preliminary Report on Patentability dated Sep. 15, 2020 in PCT Application Serial No. PCT/US2019/022009.
International Search Report and Written Opinion dated Sep. 14, 2020 in PCT Application Serial No. PCT/US2020/038523.
International Search Report and Written Opinion dated Oct. 2, 2020 in PCT Application Serial No. PCT/US2020/036107.
Schafter+Kirchhoff, Laser Beam Couplers series 60SMS for coupling into single-mode and polarization-maintaining fiber cables, Schafter+Kirchhoff, pp. 1-5, Germany.
International Search Report and Written Opinion dated Jan. 29, 2020 in PCT Application Serial No. PCT/US2020/059961.
International Search Report and Written Opinion dated Jan. 20, 2020 in PCT Application Serial No. PCT/US2020/054792.
Partial Search Report and Provisional Opinion dated Feb. 19, 2021 in PCT Application Serial No. PCT/US2020/059960.
Shariat, Mohammad H., et al. "Localization of the ectopic spiral electrical source using intracardiac electrograms during atrial fibrillation." 2015 IEEE 28th Canadian Conference on Electrical and Computer Engineering (CCECE). IEEE, 2015.
Nademanee, Koonlawee, et al. "A new approach for catheter ablation of atrial fibrillation: mapping of the electrophysiologic substrate." Journal of the American College of Cardiology 43.11 (2004): 2044-2053.
Calkins, Hugh. "Three dimensional mapping of atrial fibrillation: techniques and necessity." Journal of interventional cardiac electrophysiology 13.1 (2005): 53-59.
Shariat, Mohammad Hassan. Processing the intracardiac electrogram for atrial fibrillation ablation. Diss. Queen's University (Canada), 2016.
Meng et al., "Accurate Recovery of Atrial Endocardial Potential Maps From Non-contact Electrode Data." Auckland Bioengineering Institute. (ID 1421).
Jiang et al., "Multielectrode Catheter for Substrate Mapping for Scar-related VT Ablation: A Comparison Between Grid Versus Linear Configurations." UChicago Medicine, Center for Arrhythmia Care, Chicago IL (ID 1368).
Sacher et al., "Comparison of Manual Vs Automatic Annotation to Identify Abnormal Substrate for Scar Related VT Ablation." LIRYC Institute, Bordeaux University Hospital, France (ID 1336).
Oriel Instruments, "Introduction to Beam Splitters for Optical Research Applications", Apr. 2014, pp. 1-9, https://www.azoptics.com/Article.aspx?ArticaID=871.
International Search Report and Written Opinion dated Apr. 12, 2021 in PCT Application Serial No. PCT/US2020/059960.
International Search Report and Written Opinion dated Apr. 13, 2021 in PCT Application Serial No. PCT/US2020/064846.
International Search Report and Written Opinion dated Apr. 13, 2021 in PCT Application Serial No. PCT/US2021/013944.
International Search Report and Written Opinion dated May 25, 2021 in PCT Application Serial No. PCT/US2021/017604.
International Search Report and Written Opinion dated Jun. 2, 2021 in PCT Application Serial No. PCT/US2021/018522.
International Search Report and Written Opinion dated Jun. 2, 2021 in PCT Application Serial No. PCT/US2021/015204.
International Search Report and Written Opinion dated Jun. 17, 2021 in PCT Application Serial No. PCT/US2021/020934.
International Search Report and Written Opinion dated Jul. 13, 2021 in PCT Application Serial No. PCT/US2021/024216.
International Search Report and Written Opinion dated Jun. 22, 2021 in PCT Application Serial No. PCT/US2021/020937.
International Search Report and Written Opinion dated Jun. 24, 2021 in PCT Application Serial No. PCT/US2021/021272.

* cited by examiner

SPECTROSCOPIC TISSUE IDENTIFICATION FOR BALLOON INTRAVASCULAR LITHOTRIPSY GUIDANCE

RELATED APPLICATION

This application claims priority on U.S. Provisional Application Ser. No. 63/039,014, filed on Jun. 15, 2020. As far as permitted, the contents of U.S. Provisional Application Ser. No. 63/039,014 are incorporated in their entirety herein by reference.

BACKGROUND

Vascular lesions within vessels in the body can be associated with an increased risk for major adverse events, such as myocardial infarction, embolism, deep vein thrombosis, stroke, and the like. Severe vascular lesions, such as severely calcified vascular lesions, can be difficult to treat and achieve patency for a physician in a clinical setting.

Vascular lesions may be treated using interventions such as drug therapy, balloon angioplasty, atherectomy, stent placement, vascular graft bypass, to name a few. Such interventions may not always be ideal or may require subsequent treatment to address the lesion.

Intravascular lithotripsy is one method that has been recently used with some success for breaking up vascular lesions within vessels in the body. Intravascular lithotripsy utilizes a combination of shockwaves and bubble dynamics that are generated intravascularly in a fluid-filled balloon catheter. In particular, during a intravascular lithotripsy treatment, a high energy source is used to generate plasma and ultimately shockwaves as well as a rapid bubble expansion within a fluid-filled balloon to crack calcification at a lesion site within the vasculature. The associated rapid bubble formation from the plasma initiation and resulting localized fluid velocity within the balloon transfers mechanical energy though the incompressible fluid to impart a fracture force on the intravascular calcium, which is opposed to the balloon wall. The rapid change in fluid momentum upon hitting the balloon wall is known as hydraulic shock, or water hammer.

There is an ongoing desire to enhance vessel patency and optimization of therapy delivery parameters within a intravascular lithotripsy catheter system.

SUMMARY

The present invention is directed toward a catheter system for placement within a treatment site at a vessel wall or a heart valve. The catheter system can be used for treating a treatment site within or adjacent to the vessel wall. In various embodiments, the catheter system includes an energy source, a balloon, an energy guide, and a tissue identification system. The energy source generates energy. The balloon is positionable substantially adjacent to the treatment site, the balloon having a balloon wall that defines a balloon interior, the balloon being configured to retain a balloon fluid within the balloon interior. The energy guide is configured to receive energy from the energy source and guide the energy into the balloon interior so that plasma is formed in the balloon fluid within the balloon interior. The tissue identification system is configured to spectroscopically analyze tissue within the treatment site.

In some embodiments, the tissue identification system is configured to utilize spectroscopic tissue identification to provide real-time feedback regarding tissue type and quantity within the treatment site.

In certain embodiments, the catheter system further includes a plasma generator that is positioned at a guide distal end of the energy guide, the plasma generator being configured to generate the plasma in the balloon fluid within the balloon interior. In some embodiments, the plasma formation causes rapid bubble formation and imparts pressure waves upon the balloon wall adjacent to the treatment site.

In some embodiments, the energy source generates pulses of energy that are guided along the energy guide into the balloon interior to induce the plasma formation in the balloon fluid within the balloon interior. In one embodiment, the energy source is a laser source that provides pulses of laser energy. In certain embodiments, the energy guide can include an optical fiber. In some embodiments, the energy source is a high voltage energy source that provides pulses of high voltage. In various embodiments, the energy guide can include an electrode pair including spaced apart electrodes that extend into the balloon interior; and pulses of high voltage from the energy source can be applied to the electrodes and form an electrical arc across the electrodes.

In various embodiments, the tissue identification system includes a spectroscopic light source that is configured to provide electromagnetic energy in the form of a spectroscopic source beam that is used to diagnostically interrogate the tissue within the vascular lesion. In one embodiment, the spectroscopic light source is a broadband light source with a targeted wavelength range that is based at least in part on optical characteristics of the tissue being analyzed. In certain embodiments, the spectroscopic light source is a coherent, monochromatic light source with a targeted wavelength that is based at least in part on optical characteristics of the tissue being analyzed.

In various embodiments, the tissue identification system includes a light guide that receives the spectroscopic source beam and guides the spectroscopic source beam from a guide proximal end to a guide distal end that is positioned within the balloon interior.

In some embodiments, the tissue identification system further includes a modulator that optically couples the spectroscopic source beam into the light guide. In such embodiments, the modulator can further couple the energy from the energy source into the energy guide.

In other embodiments, the spectroscopic source beam is retained within an input fiber that is coupled to the spectroscopic light source. In one such embodiment, the input fiber is directly mechanically coupled to the light guide so that the spectroscopic source beam is optically coupled into the light guide. Alternatively, in another such embodiment, the tissue identification system further includes coupling optics so that the spectroscopic source beam is optically coupled into the light guide.

In certain embodiments, the light guide includes a plurality of guide cores; and the spectroscopic source beam is optically coupled into a first guide core of the plurality of guide cores.

In various embodiments, the light guide directs the spectroscopic source beam toward the treatment site. In one embodiment, the light guide includes a diverter that is coupled to the guide distal end to direct the spectroscopic source beam toward the treatment site.

In various embodiments, at least a portion of the spectroscopic source beam is returned by the tissue being analyzed as a returning identification beam that is directed back toward the guide distal end of the light guide. In some embodiments, the returning identification beam can be guided by the light guide from the guide distal end to the guide proximal end, and can then be directed toward a light detector that is configured to capture and quantify detected characteristics of the returning identification beam.

In some embodiments, the modulator directs the returning identification beam toward the light detector.

In certain embodiments, the returning identification beam is retained within an output fiber that is coupled to the light detector. In one such embodiment, the output fiber is directly mechanically coupled to the light guide so that the returning identification beam is optically coupled from the light guide into the output fiber. In another such embodiment, the tissue identification system further includes coupling optics so that the returning identification beam is optically coupled from the light guide into the output fiber.

In certain embodiments, the plurality of guide cores further includes a second guide core that is different than the first guide core; and the returning identification beam is optically coupled into the second guide core of the plurality of guide cores.

In various embodiments, the light detector generates a signal based on the detected characteristics of the returning identification beam and sends the signal to control electronics. Subsequently, the control electronics can analyze the signal to determine the tissue type and quantity within the treatment site.

In some embodiments, the tissue identification system utilizes at least one of specular reflectance spectroscopy, diffuse reflectance spectroscopy, fluorescence spectroscopy and Raman spectroscopy.

In various embodiments, the tissue identification system utilizes at least two of specular reflectance spectroscopy, diffuse reflectance spectroscopy, fluorescence spectroscopy and Raman spectroscopy.

The present invention is also directed toward a method for treating a treatment site within or adjacent to a vessel wall or a heart valve utilizing any of the catheter systems described herein.

In some applications, the present invention is directed toward a catheter system for treating a within or adjacent to a vessel wall, the catheter system including a light source that generates light energy; a balloon that is positionable substantially adjacent to the treatment site, the balloon having a balloon wall that defines a balloon interior, the balloon being configured to retain a balloon fluid within the balloon interior; a light guide that is configured to receive light energy from the light source and guide the light energy into the balloon interior so that plasma is formed in the balloon fluid within the balloon interior; and a tissue identification system that is configured to spectroscopically analyze tissue within the treatment site.

The present invention is also directed toward a method for treating a treatment site within or adjacent to a vessel wall or a heart valve, the method including the steps of generating energy with an energy source; positioning a balloon substantially adjacent to the treatment site, the balloon having a balloon wall that defines a balloon interior; retaining a balloon fluid within the balloon interior; receiving energy from the energy source with an energy guide; guiding the energy with the energy guide into the balloon interior so that plasma is formed in the balloon fluid within the balloon interior; and spectroscopically analyzing tissue within the treatment site with a tissue identification system.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

Figure 1:
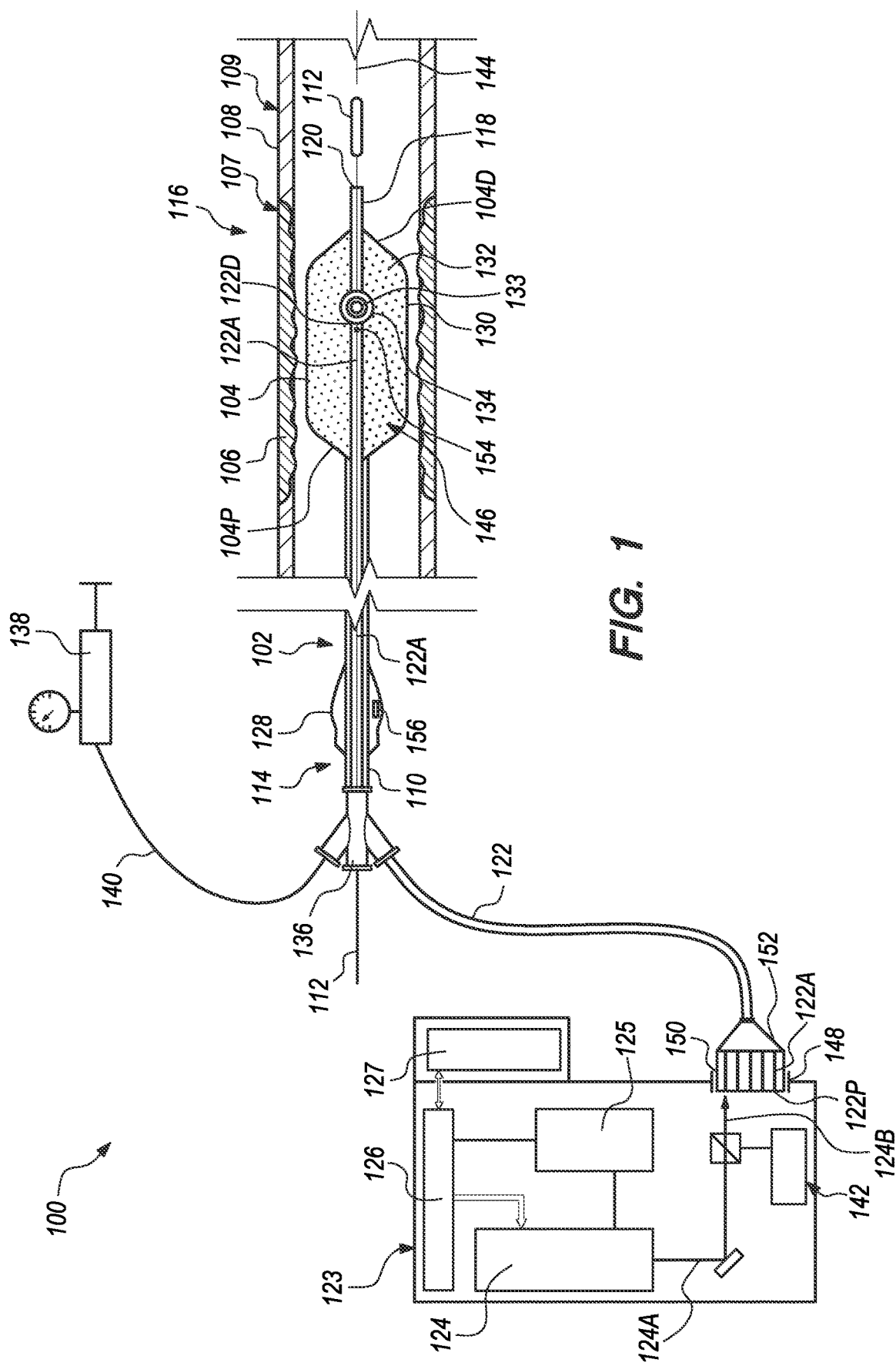
FIG. 1 is a schematic cross-sectional view of an embodiment of a catheter system in accordance with various embodiments herein, the catheter system including a tissue identification system having features of the present invention.

While embodiments of the present invention are susceptible to various modifications and alternative forms, specifics thereof have been shown by way of example and drawings, and are described in detail herein. It is understood, however, that the scope herein is not limited to the particular embodiments described. On the contrary, the intention is to cover modifications, equivalents, and alternatives falling within the spirit and scope herein.

DESCRIPTION

Treatment of vascular lesions can reduce major adverse events or death in affected subjects. As referred to herein, a major adverse event is one that can occur anywhere within the body due to the presence of a vascular lesion (also sometimes referred to herein as a treatment site. Major adverse events can include, but are not limited to, major adverse cardiac events, major adverse events in the peripheral or central vasculature, major adverse events in the brain, major adverse events in the musculature, or major adverse events in any of the internal organs.

The catheter systems and related methods disclosed herein are configured to enhance the intravascular lithotripsy therapeutic outcome by providing real-time feedback on vessel patency and optimization of the therapy delivery parameters. More particularly, the catheter systems and related methods disclosed herein include a feedback mechanism in the form of a tissue identification system that provides details on tissue type, quantity and location. Spectroscopic tissue identification methods have been demonstrated in literature, but have never been combined with a intravascular lithotripsy catheter. Utilizing ether dedicated fiber optics or existing therapy fiber optics, the intravascular lithotripsy catheter system utilizing such a tissue identification system that employs spectroscopic tissue identification can optimize treatment location and duration, energy and frequency, as well as provide therapy verification in real-time. Ultimately, a smart intravascular lithotripsy device with optical sensing, such as described herein, can improve patient outcomes while minimizing collateral damage to surrounding tissues.

In various embodiments, the catheter systems and related methods of the present invention utilize an energy source, e.g., a light source such as a laser source or another suitable energy source, which provides energy that is guided by an energy guide, e.g., in certain embodiments, a light guide, to create a localized plasma in the balloon fluid that is retained within a balloon interior of an inflatable balloon of the catheter. As such, the energy guide can sometimes be referred to as, or can be said to incorporate a "plasma generator" at or near a guide distal end of the energy guide that is positioned within the balloon interior. The creation of the localized plasma, in turn, induces a high energy bubble inside the balloon interior to create pressure waves and/or pressure waves to impart pressure onto and induce fractures in a treatment site, such as a calcified vascular lesion or a fibrous vascular lesion, at a treatment site within or adjacent to a blood vessel wall within a body of a patient. As used herein, the treatment site can include a vascular lesion such as a calcified vascular lesion or a fibrous vascular lesion, typically found in a blood vessel and/or a heart valve.

Importantly, as described in detail herein, the catheter systems of the present invention include and/or incorporate a tissue identification system that is specifically configured to provide real-time feedback on tissue type, quantity and location as a means to enhance vessel patency and optimization of the therapy delivery parameters. As described in various embodiments, the tissue identification system can provide advantages such as (i) tissue identification at the therapy location site provides an opportunity to optimize therapy parameters with the prospect of improved vessel patency, (ii) the spectroscopic identification methods are accurate and fast, with no additional procedure time required, (iii) in certain embodiments, no additional optical fibers are required, with the required optical fibers already included as part of the intravascular lithotripsy catheter system, (iv) the light source and the spectroscopic light detector of the tissue identification system are part of the reusable capital equipment, and (v) the cost of goods sold in such a single use device incorporating the tissue identification system are only negligibly increased.

In various embodiments, the catheter systems can include a catheter configured to advance to the treatment site within or adjacent a blood vessel or a heart valve within the body of the patient. The catheter includes a catheter shaft, and a balloon that is coupled and/or secured to the catheter shaft. The balloons herein can include a balloon wall that defines a balloon interior. The balloons can be configured to receive the balloon fluid within the balloon interior to expand from a deflated configuration suitable for advancing the catheter through a patient's vasculature, to an inflated configuration suitable for anchoring the catheter in position relative to the treatment site. The catheter systems also include one or more energy guides, e.g., in some embodiments, light guides, disposed along the catheter shaft and within the balloon. Each energy guide can be configured for generating pressure waves within the balloon for disrupting the vascular lesions. The catheter systems utilize energy from an energy source, e.g., light energy from a light source, to generate the plasma, i.e. via the plasma generator, within the balloon fluid at or near a guide distal end of the energy guide disposed within the balloon interior of the balloon located at the treatment site. The plasma formation can initiate a pressure wave and can initiate the rapid formation of one or more bubbles that can rapidly expand to a maximum size and then dissipate through a cavitation event that can launch a pressure wave upon collapse. The rapid expansion of the plasma-induced bubbles can generate one or more pressure waves within the balloon fluid retained within the balloon and thereby impart pressure waves upon the treatment site. In some embodiments, the energy source can be configured to provide sub-millisecond pulses of energy, e.g., light energy, from the energy source to initiate plasma formation in the balloon fluid within the balloon to cause rapid bubble formation and to impart pressure waves upon the balloon wall at the treatment site. Thus, the pressure waves can transfer mechanical energy through an incompressible balloon fluid to the treatment site to impart a fracture force on the intravascular lesion.

As used herein, the terms "intravascular lesion", "vascular lesion" or "treatment site" are used interchangeably unless otherwise noted. As such, the intravascular lesions and/or the vascular lesions are sometimes referred to herein simply as "lesions" or "treatment sites".

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it is appreciated that such a development effort might be complex and time-consuming, but would nevertheless be a routine undertaking of engineering for those of ordinary skill in the art having the benefit of this disclosure.

It is appreciated that the catheter systems disclosed herein can include many different forms. Referring now to FIG. 1, a schematic cross-sectional view is shown of a catheter system 100 in accordance with various embodiments herein. As described herein, the catheter system 100 is suitable for imparting pressure to induce fractures in one or more vascular lesions within or adjacent a vessel wall of a blood vessel or a heart valve. In the embodiment illustrated in FIG. 1, the catheter system 100 can include one or more of a catheter 102, a light guide bundle 122 including one or more light guides 122A, a source manifold 136, a fluid pump 138, a system console 123 including one or more of a light source 124, a power source 125, a system controller 126, and a graphic user interface 127 (a "GUI"), a handle assembly 128, and a tissue identification system 142. Alternatively, the catheter system 100 can have more components or fewer components than those specifically illustrated and described in relation to FIG. 1.

The catheter 102 is configured to move to a treatment site 106 within or adjacent to a blood vessel 108 within a body 107 of a patient 109. The treatment site 106 can include one or more vascular lesions such as calcified vascular lesions, for example. Additionally, or in the alternative, the treatment site 106 can include vascular lesions such as fibrous vascular lesions.

The catheter 102 can include an inflatable balloon 104 (sometimes referred to herein simply as a "balloon"), a catheter shaft 110 and a guidewire 112. The balloon 104 can be coupled to the catheter shaft 110. The balloon 104 can include a balloon proximal end 104P and a balloon distal end 104D. The catheter shaft 110 can extend from a proximal portion 114 of the catheter system 100 to a distal portion 116 of the catheter system 100. The catheter shaft 110 can include a longitudinal axis 144. The catheter shaft 110 can also include a guidewire lumen 118 which is configured to move over the guidewire 112. As utilized herein, the guidewire lumen 118 is intended to define the structure that provides a conduit through which the guidewire extends. The catheter shaft 110 can further include an inflation lumen (not shown). In some embodiments, the catheter 102 can have a distal end opening 120 and can accommodate and be tracked over the guidewire 112 as the catheter 102 is moved and positioned at or near the treatment site 106.

Importantly, as described in detail herein, the tissue identification system 142 is configured to provide real-time feedback on tissue type, quantity and location in order to effectively enhance vessel patency and optimization of therapy delivery parameters. More particularly, the tissue identification system 142 is configured to utilize optical sensing capabilities in order to improve patient outcomes while minimizing collateral damage to surrounding tissues.

The catheter shaft 110 of the catheter 102 can be coupled to the one or more light guides 122A of the light guide bundle 122 that are in optical communication with the light source 124. The light guide(s) 122A can be disposed along the catheter shaft 110 and within the balloon 104. In some embodiments, each light guide 122A can be an optical fiber and the light source 124 can be a laser. The light source 124 can be in optical communication with the light guides 122A at the proximal portion 114 of the catheter system 100.

In some embodiments, the catheter shaft 110 can be coupled to multiple light guides 122A such as a first light guide, a second light guide, a third light guide, etc., which can be disposed at any suitable positions about the guidewire lumen 118 and/or the catheter shaft 110. For example, in certain non-exclusive embodiments, two light guides 122A can be spaced apart by approximately 180 degrees about the circumference of the guidewire lumen 118 and/or the catheter shaft 110; three light guides 122A can be spaced apart by approximately 120 degrees about the circumference of the guidewire lumen 118 and/or the catheter shaft 110; or four light guides 122A can be spaced apart by approximately 90 degrees about the circumference of the guidewire lumen 118 and/or the catheter shaft 110. Still alternatively, multiple light guides 122A need not be uniformly spaced apart from one another about the circumference of the guidewire lumen 118 and/or the catheter shaft 110. More particularly, it is further appreciated that the light guides 122A described herein can be disposed uniformly or non-uniformly about the guidewire lumen 118 and/or the catheter shaft 110 to achieve the desired effect in the desired locations.

The balloon 104 can include a balloon wall 130 that defines a balloon interior 146, and can be inflated with a balloon fluid 132 to expand from a deflated configuration suitable for advancing the catheter 102 through a patient's vasculature, to an inflated configuration suitable for anchoring the catheter 102 in position relative to the treatment site 106. Stated in another manner, when the balloon 104 is in the inflated configuration, the balloon wall 130 of the balloon 104 is configured to be positioned substantially adjacent to the treatment site 106, i.e. to the vascular lesion(s). It is appreciated that although FIG. 1 illustrates the balloon wall 130 of the balloon 104 being shown spaced apart from the treatment site 106 of the blood vessel 108, this is done merely for ease of illustration, and the balloon wall 130 of the balloon 104 will typically be substantially directly adjacent to the treatment site 106 when the balloon is in the inflated configuration.

In some embodiments, the light source 124 of the catheter system 100 can be configured to provide sub-millisecond pulses of light from the light source 124, along the light guides 122A, to a location within the balloon interior 146 of the balloon 104, thereby inducing plasma formation in the balloon fluid 132 within the balloon interior 146 of the balloon 104, i.e. via a plasma generator 133 located at a guide distal end 122D of the light guide 122A. The plasma formation causes rapid bubble formation, and imparts pressure waves upon the treatment site 106. Exemplary plasma-induced bubbles are shown as bubbles 134 in FIG. 1.

It is appreciated that although the catheter systems 100 illustrated herein are generally described as including a light source 124 and one or more light guides 122A, the catheter system 100 can alternatively include any suitable energy source and energy guides for purposes of generating the desired plasma in the balloon fluid 132 within the balloon interior 146. For example, in one non-exclusive alternative embodiment, the energy source 124 can be configured to provide high voltage pulses, and each energy guide 122A can include an electrode pair including spaced apart electrodes that extend into the balloon interior 146. In such embodiment, each pulse of high voltage is applied to the electrodes and forms an electrical arc across the electrodes, which, in turn, generates the plasma and forms the pressure waves within the balloon fluid 132 that are utilized to provide the fracture force onto the vascular lesions at the treatment site 106. Still alternatively, the energy source 124 and/or the energy guides 122A can have another suitable design and/or configuration.

The balloons 104 suitable for use in the catheter systems 100 described in detail herein include those that can be passed through the vasculature of a patient when in the deflated configuration. In some embodiments, the balloons 104 herein are made from silicone. In other embodiments, the balloons 104 herein are made from polydimethylsiloxane (PDMS), polyurethane, polymers such as PEBAX™ material available from Arkema, which has a location at King of Prussia, Pennsylvania, USA, nylon, and the like. In some embodiments, the balloons 104 can include those having diameters ranging from one millimeter (mm) to 25 mm in diameter. In some embodiments, the balloons 104 can include those having diameters ranging from at least 1.5 mm to 14 mm in diameter. In some embodiments, the balloons 104 can include those having diameters ranging from at least one mm to five mm in diameter.

Additionally, in some embodiments, the balloons 104 herein can include those having a length ranging from at least three mm to 300 mm. More particularly, in some embodiments, the balloons 104 herein can include those having a length ranging from at least eight mm to 200 mm. It is appreciated that balloons 104 of greater length can be positioned adjacent to larger treatment sites 106, and, thus, may be usable for imparting pressure onto and inducing fractures in larger vascular lesions or multiple vascular lesions at precise locations within the treatment site 106. It is further appreciated that such longer balloons 104 can also be positioned adjacent to multiple treatment sites 106 at any given time.

Further, the balloons 104 herein can be inflated to inflation pressures of between approximately one atmosphere (atm) and 70 atm. In some embodiments, the balloons 104 herein can be inflated to inflation pressures of from at least 20 atm to 70 atm. In other embodiments, the balloons 104 herein can be inflated to inflation pressures of from at least six atm to 20 atm. In still other embodiments, the balloons 104 herein can be inflated to inflation pressures of from at least three atm to 20 atm. In yet other embodiments, the balloons 104 herein can be inflated to inflation pressures of from at least two atm to ten atm.

Still further, the balloons 104 herein can include those having various shapes, including, but not to be limited to, a conical shape, a square shape, a rectangular shape, a spherical shape, a conical/square shape, a conical/spherical shape, an extended spherical shape, an oval shape, a tapered shape, a bone shape, a stepped diameter shape, an offset shape, or a conical offset shape. In some embodiments, the balloons 104 herein can include a drug eluting coating or a drug eluting stent structure. The drug elution coating or drug eluting stent can include one or more therapeutic agents including anti-inflammatory agents, anti-neoplastic agents, anti-angiogenic agents, and the like.

The balloon fluid 132 can be a liquid or a gas. Exemplary balloon fluids 132 suitable for use herein can include, but are not limited to one or more of water, saline, contrast medium, fluorocarbons, perfluorocarbons, gases, such as carbon dioxide, and the like. In some embodiments, the balloon fluids 132 described can be used as base inflation fluids. In some embodiments, the balloon fluids 132 include a mixture of saline to contrast medium in a volume ratio of 50:50. In other embodiments, the balloon fluids 132 include a mixture of saline to contrast medium in a volume ratio of 25:75. In still other embodiments, the balloon fluids 132 include a mixture of saline to contrast medium in a volume ratio of 75:25. Additionally, the balloon fluids 132 suitable for use herein can be tailored on the basis of composition, viscosity, and the like in order to manipulate the rate of travel of the pressure waves therein. In certain embodiments, the balloon fluids 132 suitable for use herein are biocompatible. A volume of balloon fluid 132 can be tailored by the chosen light source 124 and the type of balloon fluid 132 used.

In some embodiments, the contrast agents used in the contrast media herein can include, but are not to be limited to, iodine-based contrast agents, such as ionic or non-ionic iodine-based contrast agents. Some non-limiting examples of ionic iodine-based contrast agents include diatrizoate, metrizoate, iothalamate, and ioxaglate. Some non-limiting examples of non-ionic iodine-based contrast agents include iopamidol, iohexol, ioxilan, iopromide, iodixanol, and ioversol. In other embodiments, non-iodine based contrast agents can be used. Suitable non-iodine containing contrast agents can include gadolinium (III)-based contrast agents. Suitable fluorocarbon and perfluorocarbon agents can include, but are not to be limited to, agents such as the perfluorocarbon dodecafluoropentane (DDFP, C5F12).

Additionally, the balloon fluids 132 herein can include those that include absorptive agents that can selectively absorb light in the ultraviolet region (e.g., at least ten nanometers (nm) to 400 nm), the visible region (e.g., at least 400 nm to 780 nm), or the near-infrared region (e.g., at least 780 nm to 2.5 µm) of the electromagnetic spectrum. Suitable absorptive agents can include those with absorption maxima along the spectrum from at least ten nm to 2.5 µm. Alternatively, the balloon fluids 132 can include those that include absorptive agents that can selectively absorb light in the mid-infrared region (e.g., at least 2.5 µm to 15 µm), or the far-infrared region (e.g., at least 15 µm to one mm) of the electromagnetic spectrum. In various embodiments, the absorptive agent can be those that have an absorption maximum matched with the emission maximum of the laser used in the catheter system 100. By way of non-limiting examples, various lasers described herein can include neodymium:yttrium-aluminum-garnet (Nd:YAG–emission maximum=1064 nm) lasers, holmium:YAG (Ho:YAG–emission maximum=2.1 µm) lasers, or erbium:YAG (Er:YAG–emission maximum=2.94 µm) lasers. In some embodiments, the absorptive agents used herein can be water soluble. In other embodiments, the absorptive agents used herein are not water soluble. In some embodiments, the absorptive agents used in the balloon fluids 132 herein can be tailored to match the peak emission of the light source 124. Various light sources 124 having emission wavelengths of at least ten nanometers to one millimeter are discussed elsewhere herein.

It is appreciated that the catheter system 100 and/or the light guide bundle 122 disclosed herein can include any number of light guides 122A in optical communication with the light source 124 at the proximal portion 114, and with the balloon fluid 132 within the balloon interior 146 of the balloon 104 at the distal portion 116. For example, in some embodiments, the catheter system 100 and/or the light guide bundle 122 can include from one light guide 122A to five light guides 122A. In other embodiments, the catheter system 100 and/or the light guide bundle 122 can include from five light guides 122A to fifteen light guides 122A. In yet other embodiments, the catheter system 100 and/or the light guide bundle 122 can include from ten light guides 122A to thirty light guides 122A. Alternatively, in still other embodiments, the catheter system 100 and/or the light guide bundle 122 can include greater than thirty light guides 122A.

The light guides 122A herein can include an optical fiber or flexible light pipe. The light guides 122A herein can be thin and flexible and can allow light signals to be sent with very little loss of strength. The light guides 122A herein can include a core surrounded by a cladding about its circumference. In some embodiments, the core can be a cylindrical core or a partially cylindrical core. The core and cladding of the light guides 122A can be formed from one or more materials, including but not limited to one or more types of glass, silica, or one or more polymers. The light guides 122A may also include a protective coating, such as a polymer. It is appreciated that the index of refraction of the core will be greater than the index of refraction of the cladding.

Each light guide 122A can guide light along its length from a proximal portion, i.e. a guide proximal end 122P, to a distal portion, i.e. the guide distal end 122D, having at least one optical window (not shown) that is positioned within the balloon interior 146. The light guides 122A can create a light path as a portion of an optical network including the light source 124. The light path within the optical network allows light to travel from one part of the network to another. Both the optical fiber and the flexible light pipe can provide a light path within the optical networks herein.

Additionally, as described in greater detail herein below, in certain embodiments, the guide distal end 122D can further include and/or incorporate a distal light receiver (not shown in FIG. 1) that enables light energy to be moved back into and through the light guide 122A from the guide distal end 122D to the guide proximal end 122P. Moreover, as described in greater detail herein below, the light energy emitted from the guide proximal end 122P after being moved back through the light guide 122A can be separated and then optically detected and/or analyzed through use of the tissue identification system 142.

Further, the light guides 122A herein can assume many configurations about and/or relative to the catheter shaft 110 of the catheters 102 described herein. In some embodiments, the light guides 122A can run parallel to the longitudinal axis 144 of the catheter shaft 110. In some embodiments, the light guides 122A can be physically coupled to the catheter shaft 110. In other embodiments, the light guides 122A can be disposed along a length of an outer diameter of the catheter shaft 110. In yet other embodiments, the light guides 122A herein can be disposed within one or more light guide lumens within the catheter shaft 110.

Additionally, it is further appreciated that the light guides 122A can be disposed at any suitable positions about the circumference of the guidewire lumen 118 and/or the catheter shaft 110, and the guide distal end 122D of each of the light guides 122A can be disposed at any suitable longitudinal position relative to the length of the balloon 104 and/or relative to the length of the guidewire lumen 118.

Further, the light guides 122A herein can include one or more photoacoustic transducers 154, where each photoacoustic transducer 154 can be in optical communication with the light guide 122A within which it is disposed. In some embodiments, the photoacoustic transducers 154 can be in optical communication with the guide distal end 122D of the light guide 122A. Additionally, in such embodiments, the photoacoustic transducers 154 can have a shape that corresponds with and/or conforms to the guide distal end 122D of the light guide 122A.

The photoacoustic transducer 154 is configured to convert light energy into an acoustic wave at or near the guide distal end 122D of the light guide 122A. It is appreciated that the direction of the acoustic wave can be tailored by changing an angle of the guide distal end 122D of the light guide 122A.

It is further appreciated that the photoacoustic transducers 154 disposed at the guide distal end 122D of the light guide 122A herein can assume the same shape as the guide distal end 122D of the light guide 122A. For example, in certain non-exclusive embodiments, the photoacoustic transducer 154 and/or the guide distal end 122D can have a conical shape, a convex shape, a concave shape, a bulbous shape, a square shape, a stepped shape, a half-circle shape, an ovoid shape, and the like. It is also appreciated that the light guide 122A can further include additional photoacoustic transducers 154 disposed along one or more side surfaces of the length of the light guide 122A.

The light guides 122A described herein can further include one or more diverting features or "diverters" (not shown in FIG. 1) within the light guide 122A that are configured to direct light to exit the light guide 122A toward a side surface e.g., at or near the guide distal end 122D of the light guide 122A, and toward the balloon wall 130. A diverting feature can include any feature of the system herein that diverts light from the light guide 122A away from its axial path toward a side surface of the light guide 122A. Additionally, the light guides 122A can each include one or more light windows disposed along the longitudinal or circumferential surfaces of each light guide 122A and in optical communication with a diverting feature. Stated in another manner, the diverting features herein can be configured to direct light in the light guide 122A toward a side surface, e.g., at or near the guide distal end 122D, where the side surface is in optical communication with a light window. The light windows can include a portion of the light guide 122A that allows light to exit the light guide 122A from within the light guide 122A, such as a portion of the light guide 122A lacking a cladding material on or about the light guide 122A.

Examples of the diverting features suitable for use herein include a reflecting element, a refracting element, and a fiber diffuser. Additionally, the diverting features suitable for focusing light away from the tip of the light guides 122A herein can include, but are not to be limited to, those having a convex surface, a gradient-index (GRIN) lens, and a mirror focus lens. Upon contact with the diverting feature, the light is diverted within the light guide 122A to the plasma generator 133 and/or the photoacoustic transducer(s) 154 that are in optical communication with a side surface of the light guide 122A. As noted, the plasma generator 133 and/or the photoacoustic transducer(s) 154 then convert light energy into an acoustic pressure wave and bubble that extend away from the side surface of the light guide 122A.

The source manifold 136 can be positioned at or near the proximal portion 114 of the catheter system 100. The source manifold 136 can include one or more proximal end openings that can receive the plurality of light guides 122A of the light guide bundle 122, the guidewire 112, and/or an inflation conduit 140 that is coupled in fluid communication with the fluid pump 138. The catheter system 100 can also include the fluid pump 138 that is configured to inflate the balloon 104 with the balloon fluid 132, i.e. via the inflation conduit 140, as needed.

As noted above, in the embodiment illustrated in FIG. 1, the system console 123 includes one or more of the light source 124, the power source 125, the system controller 126, and the GUI 127. Alternatively, the system console 123 can include more components or fewer components than those specifically illustrated in FIG. 1. For example, in certain non-exclusive alternative embodiments, the system console 123 can be designed without the GUI 127. Still alternatively, one or more of the light source 124, the power source 125, the system controller 126, and the GUI 127 can be provided within the catheter system 100 without the specific need for the system console 123.

Further, as illustrated in FIG. 1, in certain embodiments, at least a portion of the tissue identification system 142 can also be positioned substantially within the system console 123. Alternatively, components of the tissue identification system 142 can be positioned in a different manner than what is specifically shown in FIG. 1.

Additionally, as shown, the system console 123, and the components included therewith, is operatively coupled to the catheter 102, the light guide bundle 122, and the remainder of the catheter system 100. For example, in some embodiments, as illustrated in FIG. 1, the system console 123 can include a console connection aperture 148 (also sometimes referred to generally as a "socket") by which the light guide bundle 122 is mechanically coupled to the system console 123. In such embodiments, the light guide bundle 122 can include a guide coupling housing 150 (also sometimes referred to generally as a "ferrule") that houses a portion, e.g., the guide proximal end 122P, of each of the light guides 122A. The guide coupling housing 150 is configured to fit and be selectively retained within the console connection aperture 148 to provide the desired mechanical coupling between the light guide bundle 122 and the system console 123.

Further, the light guide bundle 122 can also include a guide bundler 152 (or "shell") that brings each of the individual light guides 122A closer together so that the light guides 122A and/or the light guide bundle 122 can be in a more compact form as it extends with the catheter 102 into the blood vessel 108 during use of the catheter system 100.

As provided herein, the light source 124 can be selectively and/or alternatively coupled in optical communication with each of the light guides 122A, i.e. to the guide proximal end 122P of each of the light guides 122A, in the light guide bundle 122. In particular, the light source 124 is configured to generate light energy in the form of a source beam 124A, e.g., a pulsed source beam that can be selectively and/or alternatively directed to and received by each of the light guides 122A in the light guide bundle 122 as an individual guide beam 124B. Alternatively, the catheter system 100 can include more than one light source 124. For example, in one non-exclusive alternative embodiment, the catheter system 100 can include a separate light source 124 for each of the light guides 122A in the light guide bundle 122.

The light source 124 can have any suitable design. In certain embodiments, as noted above, the light source 124 can be configured to provide sub-millisecond pulses of light from the light source 124 that are focused onto a small spot in order to couple it into the guide proximal end 122P of the light guide 122A. Such pulses of light energy are then directed along the light guides 122A to a location within the balloon 104, thereby inducing plasma formation in the balloon fluid 132 within the balloon interior 146 of the balloon 104. In particular, the light energy emitted at the guide distal end 122D of the light guide 122A energizes the plasma generator 133 to form the plasma within the balloon fluid 132 within the balloon interior 146. The plasma formation causes rapid bubble formation, and imparts pressure waves upon the treatment site 106. In such embodiments, the sub-millisecond pulses of light from the light source 124 can be delivered to the treatment site 106 at a frequency of between approximately one hertz (Hz) and 5000 Hz. In some embodiments, the sub-millisecond pulses of light from the light source 124 can be delivered to the treatment site 106 at a frequency of between approximately 30 Hz and 1000 Hz. In other embodiments, the sub-millisecond pulses of light from the light source 124 can be delivered to the treatment site 106 at a frequency of between approximately ten Hz and 100 Hz. In yet other embodiments, the sub-millisecond pulses of light from the light source 124 can be delivered to the treatment site 106 at a frequency of between approximately one Hz and 30 Hz. Alternatively, the sub-millisecond pulses of light can be delivered to the treatment site 106 at a frequency that can be greater than 5000 Hz.

It is appreciated that although the light source 124 is typically utilized to provide pulses of light energy, the light source 124 can still be described as providing a single source beam 124A, i.e. a single pulsed source beam.

The light sources 124 suitable for use herein can include various types of light sources including lasers and lamps. Alternatively, as noted above, the light sources 124, as referred to herein, can include any suitable type of energy source.

Suitable lasers can include short pulse lasers on the sub-millisecond timescale. In some embodiments, the light source 124 can include lasers on the nanosecond (ns) timescale. The lasers can also include short pulse lasers on the picosecond (ps), femtosecond (fs), and microsecond (us) timescales. It is appreciated that there are many combinations of laser wavelengths, pulse widths and energy levels that can be employed to achieve plasma in the balloon fluid 132 of the catheters 102 described herein. In various embodiments, the pulse widths can include those falling within a range including from at least ten ns to 3000 ns. In some embodiments, the pulse widths can include those falling within a range including from at least 20 ns to 100 ns. In other embodiments, the pulse widths can include those falling within a range including from at least one ns to 500 ns.

Additionally, exemplary nanosecond lasers can include those within the UV to IR spectrum, spanning wavelengths of about ten nanometers (nm) to one millimeter (mm). In some embodiments, the light sources 124 suitable for use in the catheter systems 100 herein can include those capable of producing light at wavelengths of from at least 750 nm to 2000 nm. In other embodiments, the light sources 124 can include those capable of producing light at wavelengths of from at least 700 nm to 3000 nm. In still other embodiments, the light sources 124 can include those capable of producing light at wavelengths of from at least 100 nm to ten micrometers (μm). Nanosecond lasers can include those having repetition rates of up to 200 kHz. In some embodiments, the laser can include a Q-switched thulium:yttrium-aluminum-garnet (Tm:YAG) laser. In other embodiments, the laser can include a neodymium:yttrium-aluminum-garnet (Nd:YAG) laser, holmium:yttrium-aluminum-garnet (Ho:YAG) laser, erbium:yttrium-aluminum-garnet (Er:YAG) laser, excimer laser, helium-neon laser, carbon dioxide laser, as well as doped, pulsed, fiber lasers.

The catheter systems 100 disclosed herein can generate pressure waves having maximum pressures in the range of at least one megapascal (MPa) to 100 MPa. The maximum pressure generated by a particular catheter system 100 will depend on the light source 124, the absorbing material, the bubble expansion, the propagation medium, the balloon material, and other factors. In some embodiments, the catheter systems 100 herein can generate pressure waves having maximum pressures in the range of at least two MPa to 50 MPa. In other embodiments, the catheter systems 100 herein can generate pressure waves having maximum pressures in the range of at least two MPa to 30 MPa. In yet other embodiments, the catheter systems 100 herein can generate pressure waves having maximum pressures in the range of at least 15 MPa to 25 MPa.

The pressure waves described herein can be imparted upon the treatment site 106 from a distance within a range from at least 0.1 millimeters (mm) to 25 mm extending radially from the light guides 122A when the catheter 102 is placed at the treatment site 106. In some embodiments, the pressure waves can be imparted upon the treatment site 106 from a distance within a range from at least ten mm to 20 mm extending radially from the light guides 122A when the catheter 102 is placed at the treatment site 106. In other embodiments, the pressure waves can be imparted upon the treatment site 106 from a distance within a range from at least one mm to ten mm extending radially from the light guides 122A when the catheter 102 is placed at the treatment site 106. In yet other embodiments, the pressure waves can be imparted upon the treatment site 106 from a distance within a range from at least 1.5 mm to four mm extending radially from the light guides 122A when the catheter 102 is placed at the treatment site 106. In some embodiments, the pressure waves can be imparted upon the treatment site 106 from a range of at least two MPa to 30 MPa at a distance from 0.1 mm to ten mm. In some embodiments, the pressure waves can be imparted upon the treatment site 106 from a range of at least two MPa to 25 MPa at a distance from 0.1 mm to ten mm.

The power source 125 is electrically coupled to and is configured to provide necessary power to each of the light source 124, the system controller 126, the GUI 127, the handle assembly 128, and the tissue identification system 142. The power source 125 can have any suitable design for such purposes.

As noted, the system controller 126 is electrically coupled to and receives power from the power source 125. Additionally, the system controller 126 is coupled to and is configured to control operation of each of the light source 124, the GUI 127 and the tissue identification system 142. The system controller 126 can include one or more processors or circuits for purposes of controlling the operation of at least the light source 124, the GUI 127 and the tissue identification system 142. For example, the system controller 126 can control the light source 124 for generating pulses of light energy as desired, e.g., at any desired firing rate. Additionally, the system controller 126 can control and/or operate in conjunction with the tissue identification system 142 to effectively provide real-time feedback regarding the type, size and location of any tissue at or near the treatment site 106 in order to optimize treatment in real-time.

Additionally, the system controller 126 can further be configured to control operation of other components of the catheter system 100, e.g., the positioning of the catheter 102 adjacent to the treatment site 106, the inflation of the balloon 104 with the balloon fluid 132, etc. Further, or in the alternative, the catheter system 100 can include one or more additional controllers that can be positioned in any suitable manner for purposes of controlling the various operations of the catheter system 100. For example, in certain embodiments, an additional controller and/or a portion of the system controller 126 can be positioned and/or incorporated within the handle assembly 128.

The GUI 127 is accessible by the user or operator of the catheter system 100. Additionally, the GUI 127 is electrically connected to the system controller 126. With such design, the GUI 127 can be used by the user or operator to ensure that the catheter system 100 is employed as desired to impart pressure onto and induce fractures into the vascular lesions at the treatment site 106. Additionally, the GUI 127 can provide the user or operator with information that can be used before, during and after use of the catheter system 100. In one embodiment, the GUI 127 can provide static visual data and/or information to the user or operator. In addition, or in the alternative, the GUI 127 can provide dynamic visual data and/or information to the user or operator, such as video data or any other data that changes over time, e.g., during use of the catheter system 100. Further, in various embodiments, the GUI 127 can include one or more colors, different sizes, varying brightness, etc., that may act as alerts to the user or operator. Additionally, or in the alternative, the GUI 127 can provide audio data or information to the user or operator. It is appreciated that the specifics of the GUI 127 can vary depending upon the design requirements of the catheter system 100, or the specific needs, specifications and/or desires of the user or operator.

As shown in FIG. 1, the handle assembly 128 can be positioned at or near the proximal portion 114 of the catheter system 100, and/or near the source manifold 136. Additionally, in this embodiment, the handle assembly 128 is coupled to the balloon 104 and is positioned spaced apart from the balloon 104. Alternatively, the handle assembly 128 can be positioned at another suitable location.

The handle assembly 128 is handled and used by the user or operator to operate, position and control the catheter 102. The design and specific features of the handle assembly 128 can vary to suit the design requirements of the catheter system 100. In the embodiment illustrated in FIG. 1, the handle assembly 128 is separate from, but in electrical and/or fluid communication with one or more of the system controller 126, the light source 124, the fluid pump 138, the GUI 127 and the tissue identification system 142. In some embodiments, the handle assembly 128 can integrate and/or include at least a portion of the system controller 126 within an interior of the handle assembly 128. For example, as shown, in certain such embodiments, the handle assembly 128 can include circuitry 156 that can form at least a portion of the system controller 126. Additionally, in some embodiments, the circuitry 156 can receive electrical signals or data from the tissue identification system 142. Further, or in the alternative, the circuitry 156 can transmit such electrical signals or otherwise provide data to the system controller 126.

In one embodiment, the circuitry 156 can include a printed circuit board having one or more integrated circuits, or any other suitable circuitry. In an alternative embodiment, the circuitry 156 can be omitted, or can be included within the system controller 126, which in various embodiments can be positioned outside of the handle assembly 128, e.g., within the system console 123. It is understood that the handle assembly 128 can include fewer or additional components than those specifically illustrated and described herein.

As noted above, and as provided in greater detail herein below, the tissue identification system 142 is configured to utilize spectroscopic tissue identification and analysis to effectively provide real-time feedback regarding the type, size, quantity and location of any tissue at or near the treatment site 106 in order to optimize treatment in real-time. Additionally, it is further appreciated that the tissue identification system 142 can have any suitable design and/or use any suitable types of spectroscopic methodologies for purposes of providing the desired real-time feedback regarding the type, size, quantity and location of any tissue at or near the treatment site 106 in order to optimize treatment in real-time.

Spectroscopy is a genre of optical sensing methods. When light interacts with tissue, there are a multitude of optical properties that affect the light propagation path, wavelength, and energy state. Reflection, refraction, absorbance, scattering, anisotropy, phase change, and fluorescent properties of tissues are all elements that affect the trajectory, wavelength, and intensity of the photons in the tissue.

In certain non-exclusive embodiments of the present invention, the tissue identification system 142 can utilize one or more of specular reflectance spectroscopy, diffuse reflectance spectroscopy, fluorescence spectroscopy, and Raman spectroscopy, which have each been utilized to exploit differences in optical properties and discriminate between tissue types. Additionally, or in the alternative, the tissue identification system 142 can utilize one or more other types of spectroscopy in order to provide the desired real-time feedback regarding the type, size, quantity and location of any tissue at or near the treatment site 106 in order to optimize treatment in real-time.

Specular reflectance spectroscopy is designed to measure the reflecting efficiency of the tissue being analyzed, i.e. by analyzing the light that is purely reflected off the surface of the tissue. Diffuse reflectance spectroscopy (DRS) is designed to measure the scattering effect of the tissue as a function of the light wavelength. More particularly, DRS projects a specific band of light (band size and wavelength dependent on tissue target) light into the tissue at a specific point(s) and collects the intensity of backscattered light at another specific location, returning this signal to a spectrometer to reconstruct the spectra of scattered light. Fluorescence spectroscopy is designed to recognize a specific wavelength of light that excites endogenous fluorophores found in intracellular molecules and tissue matrix molecules to an elevated singlet state. The energy in the fluorophore is then emitted at a higher wavelength of light as the fluorophore decays back to its ground state. Raman spectroscopy is designed to utilize excitation light of a specific wavelength that enters the tissue and induces a dipole amongst the molecule's electrons via non-elastic scattering. The molecule then emits radiation at the dipole oscillating frequency. This signal can be very small, but it is directly correlated to the chemical bond strength of molecules found in the biological environment. The information given by Raman spectroscopy is very similar to the information from a chemical assay and enables chemical characterization of tissue.

Certain non-exclusive examples of potential designs for the tissue identification system 142 are described in detail herein below.

Figure 2:
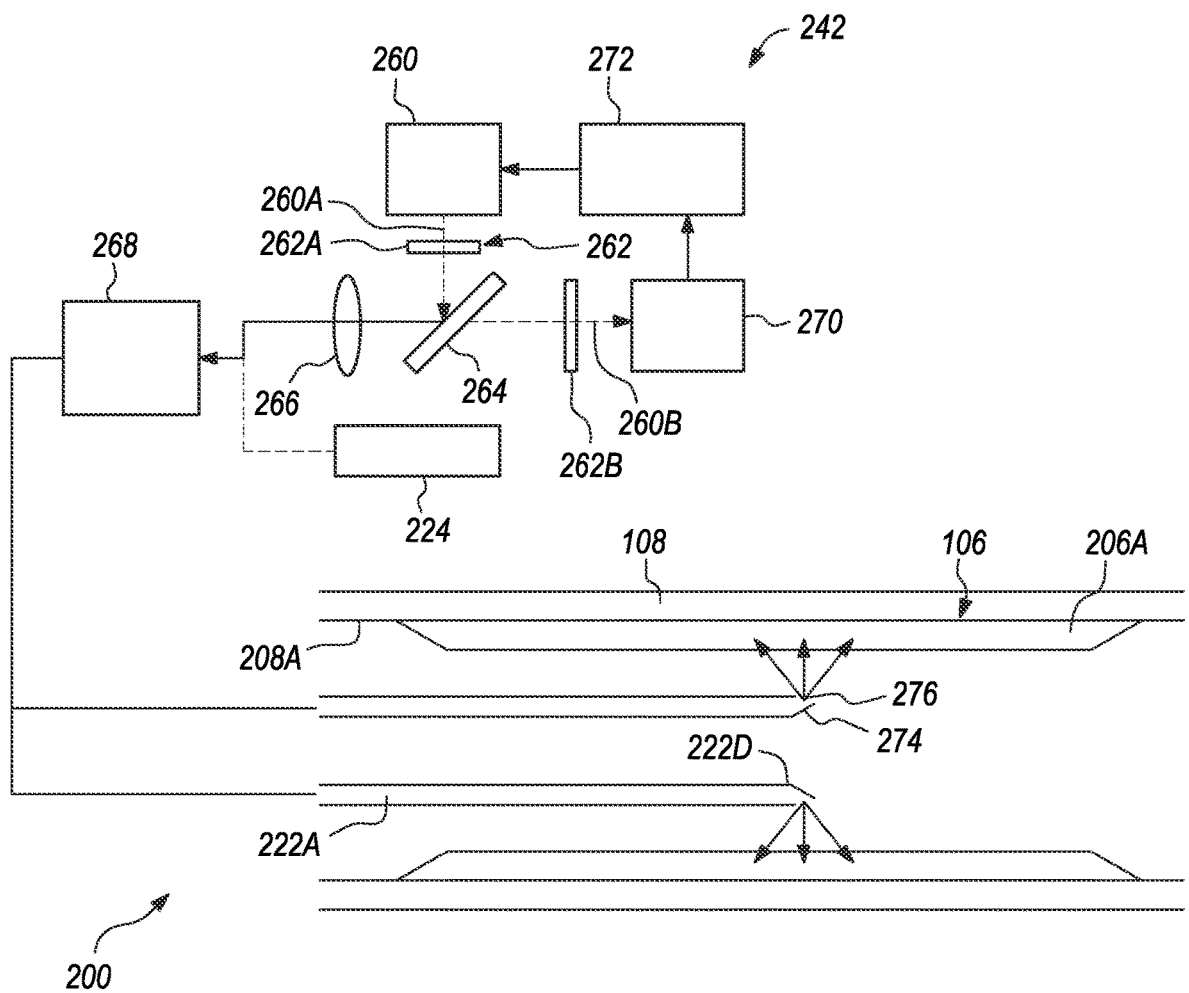
FIG. 2 is a simplified schematic view of a portion of an embodiment of the catheter system including an embodiment of the tissue identification system.

FIG. 2 is a simplified schematic view of a portion of an embodiment of the catheter system 200 including an embodiment of the tissue identification system 242. The design of the catheter system 200 is substantially similar to the embodiments illustrated and described herein above. It is appreciated that various components of the catheter system 200, such as are shown in FIG. 1, are not illustrated in FIG. 2 for purposes of clarity and ease of illustration. However, it is appreciated that the catheter system 200 will likely include most, if not all, of such components.

As shown in FIG. 2, the catheter system 200 again at least includes an energy source 224, e.g., a light source or other suitable energy source, and one or more energy guides 222A, e.g., light guides or other suitable energy guides. As above, the energy guides 222A are configured to guide energy from the energy source 224 into the balloon interior 146 (illustrated in FIG. 1) to generate plasma within the balloon fluid 132 (illustrated in FIG. 1) at or near a guide distal end 222D of the energy guide 222A disposed within the balloon interior 146 of the balloon 104 (illustrated in FIG. 1), which can be located at a treatment site 106 including a vascular lesion 206A within and/or adjacent to a vessel wall 208A of a blood vessel 108. Further, as above, the plasma formation can initiate a pressure wave and can initiate the rapid formation of one or more bubbles that can rapidly expand to a maximum size and then dissipate through a cavitation event that can launch a pressure wave upon collapse. The rapid expansion of the plasma-induced bubbles can generate one or more pressure waves within the balloon fluid 132 retained within the balloon 104 and thereby impart pressure waves upon the treatment site 106.

Additionally, as noted, FIG. 2 also shows an embodiment of the tissue identification system 242 that is configured to utilize one or more spectroscopic tissue identification methodologies to identify the type, size, quantity and location of any tissue at or near the treatment site 106 in order to optimize treatment in real-time. The tissue identification system 242 can have any suitable configuration pursuant to the requirements of the catheter system 200. In certain embodiments, as shown in FIG. 2, the tissue identification system 242 can include one or more of a spectroscopic light source 260, a filter assembly 262, a beamsplitter 264, an optical element 266, a modulator 268, a light detector 270 and control electronics 272. Additionally, the tissue identification system 242 can further include one or more light guides 222A, which can be the same light guides 222A that are used to direct the energy from the energy source 224, or can be dedicated light guides 222A that are used only for purposes of tissue identification. Further, or in the alternative, the tissue identification system 242 can include more components or fewer components than those specifically illustrated in FIG. 2.

As described herein, it is appreciated that certain features and components of the tissue identification system 242 can be modified depending upon the specific type of spectroscopy being utilized within the catheter system 200. For example, the design and/or operation of the spectroscopic light source 260, the filter assembly 262, the beamsplitter 264, the modulator 268 and the light detector 270 can be modified depending on the particular spectroscopic methodologies being used at any given time within the catheter system 200.

The spectroscopic light source 260 is configured to provide electromagnetic energy in the form of a spectroscopic source beam 260A that is used to diagnostically interrogate the tissue of interest, e.g., within the vascular lesion 206A at the treatment site 106. In certain alternative embodiments, the spectroscopic light source 260 can be either a coherent laser source of a specific targeted wavelength (such as is required for fluorescence spectroscopy and Raman spectroscopy), or a broadband light source with a targeted wavelength range.

For example, when employing specular reflectance spectroscopy, the spectroscopic light source 260 can be a broadband light source, which can use a halogen, deuterium, xenon, or tungsten lamp, white LED, or a monochromatic (laser) light source with a wavelength depending on the optical characteristics of the tissue of interest. Similarly, when employing diffuse reflectance spectroscopy, the spectroscopic light source 260 can also be a broadband light source, which can use a halogen, deuterium, xenon or tungsten lamp, white LED, or some combination thereof. Conversely, when employing either fluorescence spectroscopy or Raman spectroscopy, the spectroscopic light source 260 can be a monochromatic light source (usually a laser source) that is based on the characteristics (fluorescent characteristics in the case of fluorescence spectroscopy) of the tissue of interest.

As shown in FIG. 2, the spectroscopic source beam 260A from the spectroscopic light source 260 can be initially directed toward a first filter 262A of the filter assembly 262. The first filter 262A is an optical device that is configured to only transmit light in a specific wavelength range or polarity. It is appreciated that the use of the first filter 262A enables targeted interrogation and detection based on the optical characteristics of the tissue(s) of interest for optimum identification.

Subsequently, the spectroscopic source beam 260A is directed toward the beamsplitter 264, which splits the spectroscopic source beam 260A and reflects at least a portion of the spectroscopic source beam 260A so that it is directed toward the optical element 266. As utilized in the tissue identification system 242, the beamsplitter 264 is configured to split the spectroscopic source beam 260A and a returning identification beam 260B (as described herein below) so that both beams 260A, 260B can be coupled into the same light guide 222A.

The portion of the spectroscopic source beam 260A that is directed toward the optical element 266, e.g., a focusing lens, is focused by the optical element 266 in order to couple the spectroscopic source beam 260A into one of the light guides 222A with optimum transmission.

As shown, prior to being coupled into one of the light guides 222A, the spectroscopic source beam 260A is directed toward the modulator 268, e.g., an optical switch or splitter. As used in the tissue identification system 242, the modulator 268 is an optical device that enables multiple optical inputs to travel down one optical fiber, i.e. one light guide 222A, by mechanically modulating the physical connections. More particularly, as illustrated, the modulator 268 enables the therapeutic pulsed beams from the energy source 224 to travel down the same optical fiber, i.e. the same light guide 222A, that is used for transmitting the spectroscopic source beam 260A for sensing the tissue between each pulse of the energy source 224. Additionally, the modulator 268 also enables multiple tissue identification methodologies to be used with the same light guide 222A.

As noted, the modulator 268 couples the spectroscopic source beam 260A into the guide proximal end of the desired light guide 222A, which guides the spectroscopic source beam 260A into the balloon interior 146. Additionally, as illustrated, in certain embodiments, the light guide 222A can include a diverter 274 that is positioned at or near the guide distal end 222D of the light guide 222A and that is configured to more accurately and precisely direct the spectroscopic source beam 260A toward the tissue of interest, e.g., the vascular lesion 206A that is present at the treatment site 106 within and/or adjacent to the vessel wall 208A of the blood vessel 108.

Depending upon the particular spectroscopic methodology being employed during any given use of the tissue identification system 242, at least a portion of the spectroscopic source beam 260A is returned, e.g., reflected, refracted, scattered, phase changed, fluoresced, etc., by the tissue based on the properties of the tissue and is directed back toward the guide distal end 222D of the light guide 222A as the returning identification beam 260B. More specifically, the returning identification beam 260B can be received back into the guide distal end 222D of the light guide 222A via a distal light receiver 276 that is coupled to the guide distal end 222D of the light guide 222A.

Thus, in certain embodiments, the light guide 222A can be a thin and flexible optical fiber that can be used to both introduce the spectroscopic source beam 260A to the tissue of interest and collect the return spectra in the form of the returning identification beam 260B. Additionally, it is appreciated that different fiber tip geometries, i.e. different diverters 274, as well as fiber gratings, can be used to direct and focus the light as desired. Alternatively, in other embodiments, different light guides 222A can be used for introducing the spectroscopic source beam 260A to the tissue of interest and collecting the return spectra in the form of the returning identification beam 260B.

Further, as described in detail herein below, in certain embodiments, the light guides 222A can have a unique design, e.g., using a multicore optical fiber with two or more cores, to enable the light guides 222A to more effectively both introduce the spectroscopic source beam 260A to the tissue of interest and collect the return spectra in the form of the returning identification beam 260B.

The returning identification beam 260B is then guided back through the light guide 222A from the guide distal end 222D to the guide proximal end before being directed back toward and through the modulator 268. The returning identification beam 260B is then directed back through the optical element 266 before being directed toward the beamsplitter 264. The beamsplitter 264 then transmits at least a portion of the returning identification beam 260B, depending on the characteristics of the returning identification beam 260B and the design of the beamsplitter 264, toward a second filter 262B of the filter assembly 262. As with the first filter 262A, the second filter 262B is an optical device that is configured to only transmit light in a specific wavelength range or polarity. Thus, the desired portion of the returning identification beam 260B, which is selected based on the particular spectroscopic methodology being utilized at any given time, is directed to the light detector 270.

The light detector 270 is configured to capture and quantify the characteristics of the returning identification beam 260B that has returned from the tissue of interest. The light detector 270 may also separate and quantify the light within the returning identification beam 260B by wavelength. More specifically, the light detector 270 can be provided in the form of a spectrometer that can separate the light of the returning identification beam 260B into discrete wavelengths and then measure the intensity of each wavelength. The light detector 270 can then generate an appropriate signal based on the detected characteristics and measured wavelength intensity of the returning identification beam 260B which is then sent to the control electronics 272.

The control electronics 272, which can form a portion of the system controller 126 (illustrated in FIG. 1) or which can be provided separately from the system controller 126 and can be in electrical communication with the system controller 126, analyzes the signal from the light detector 270 to provide an effective determination regarding the type, size, quantity and location of any tissue at or near the treatment site 106 in order to optimize treatment in real-time. More specifically, the control electronics 272 utilize an appropriate algorithm to effectively identify tissue type, size and location. Further, it is appreciated that the algorithm can be more robust if and when multiple spectroscopic methodologies are utilized.

With the design of the tissue identification system 242 and/or the catheter system 200, as described in detail herein, the tissue identification system 242 is able to provide an initial analysis of the tissue type, size and location at the treatment site 106, and also to provide a continuous sensing of the tissue type, size and location to monitor the efficacy of the intravascular lithotripsy procedure in real-time.

As noted above, in any given use and application of the tissue identification system 242, the tissue identification system 242 can utilize one or more of specular reflectance spectroscopy, diffuse reflectance spectroscopy, fluorescence spectroscopy, and Raman spectroscopy, or another spectroscopic methodology to provide an effective determination regarding the type, size, quantity and location of any tissue at or near the treatment site 106. It is appreciated that certain methodologies have better sensitivity for different tissue types. Thus, the tissue identification system 242 can have better overall modality by combining two or more of the noted methodologies. Accordingly, any such combination of methodologies can provide increased fidelity in sensing options. Additionally, or in the alternative, the use of multiple methodologies can serve as a self-check to see if each methodology provides the same analysis.

Additionally, as also noted above, it is appreciated that certain features and components of the tissue identification system 242 can be modified depending upon the specific type of spectroscopy being utilized within the catheter system 200.

For example, when utilizing specular reflectance spectroscopy, the spectroscopic light source 260, as noted, could be broadband (halogen, deuterium, xenon, or tungsten lamp, white LED) or monochromatic (laser) light with a wavelength depending on the optical characteristics of the tissue of interest. Additionally, for the light detector 270, the detection characteristics are dictated by the optical tissue of interest (wavelengths at which it is the most different from the surrounding tissues) and the wavelength(s) of the spectroscopic light source 260. This could be a fairly wide range of wavelengths, or a very specific wavelength. In some embodiments, detection could be done by a CCD spectrometer, a photodiode with the proper filters, or a similar device. Further, specular reflectance spectroscopy may also use a light polarizer and a polarization filter, as reflected polarized light maintains polarization while light that transmits below the surface of the tissue and returns to the surface loses its polarization.

When utilizing diffuse reflectance spectroscopy, the spectroscopic light source 260, as noted, can be broadband (halogen, deuterium, xenon, or tungsten lamp, white LED or some combination thereof). Additionally, for the light detector 270, the detection characteristics are again dictated by the optical tissue of interest (wavelengths at which it is the most different from the surrounding tissues) and the wavelength(s) of the spectroscopic light source 260. This could be a fairly wide range of wavelengths, or a very specific wavelength. Again, in some embodiments, detection could be done by a CCD spectrometer, a photodiode with the proper filters, or a similar device.

When utilizing fluorescence spectroscopy, as noted, the spectroscopic light source 260 can utilize monochromatic light (usually laser) based on the fluorescent characteristics of the tissue of interest. Additionally, the light detector 270 can be configured to focus on a small, specific wavelength range based on the fluorescent characteristics of the tissue of interest.

When utilizing Raman spectroscopy, as noted, the spectroscopic light source 260 can be a monochromatic light (usually laser) based on the characteristics of the tissue of interest. Additionally, the light detector 270 can be configured to focus on a wide spectral range, and may require high sensitivity sensing elements for the small signals. Further, in some such embodiments, the tissue identification system 242 may also require a laser rejection filter to selectively transmit only Raman scattered light.

Additionally, it is appreciated that, in certain embodiments, beyond spectroscopic tissue identification methods, the light guides 222A in the catheter system 200 could also be utilized for optical imaging modalities. For example, in some non-exclusive alternative embodiments, the light guides 222A can further be used for optical coherence tomography (OCT) and/or optical coherence elastography (OCE). In OCT, images are created by mapping the scattering properties of tissue. This method requires focusing optics and a reference to create the coherence interference signal. Additionally, chirped pulse interferometry, which is an extension of OCT, can also be utilized which entails imaging using oppositely-chirped laser pulses in order to avoid dispersion (providing more depth penetration). In OCE, images are created by mapping the mechanical properties of a tissue. This method requires an applied force (balloon or possible acoustic/mechanical forces from pulsed laser) and an OCT imaging system. OCE data and images could be used to identify different plaque types before and after a intravascular lithotripsy procedure.

Figure 3:
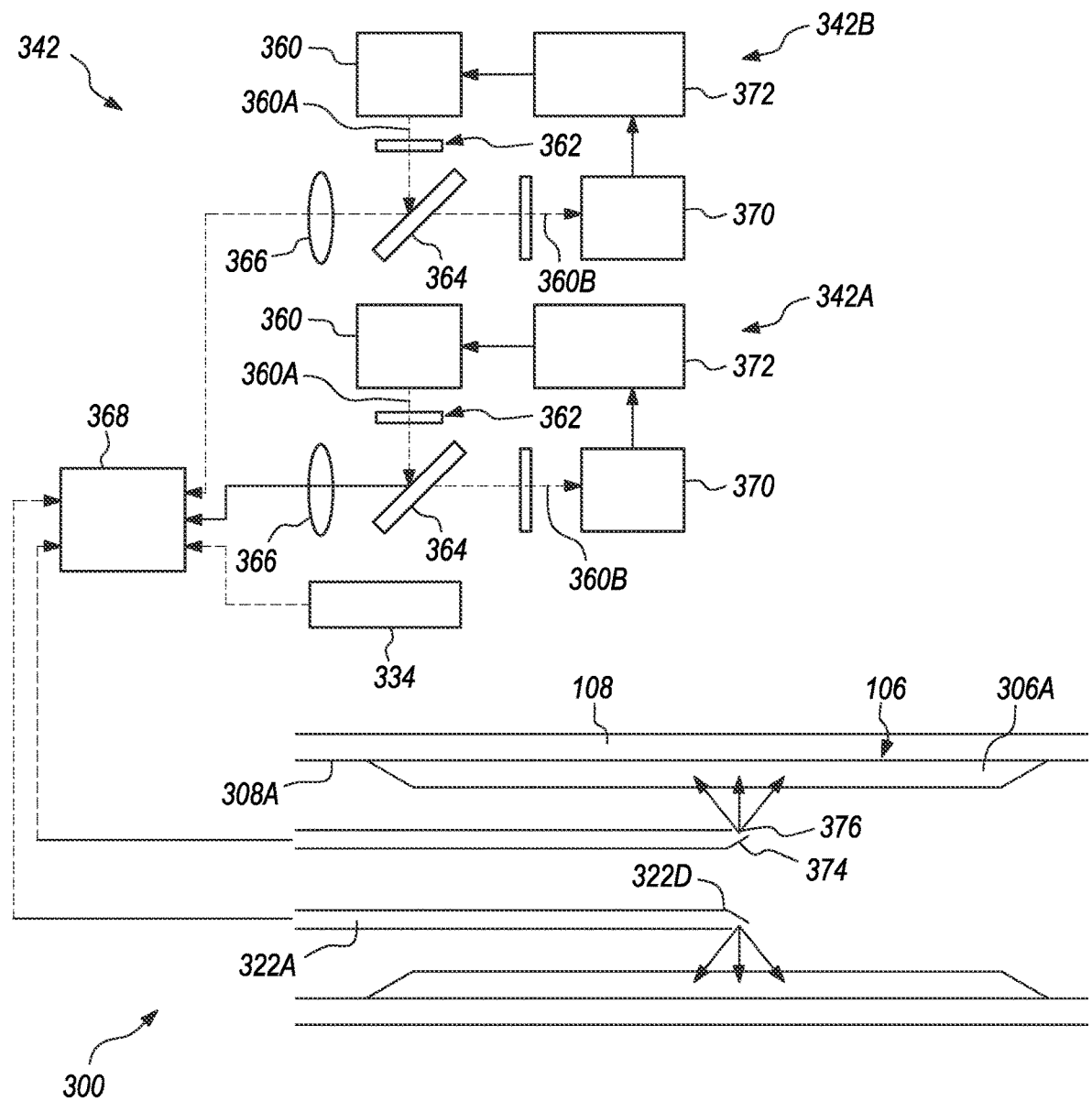
FIG. 3 is a simplified schematic view of a portion of another embodiment of the catheter system including another embodiment of the tissue identification system.

It is appreciated that the combining of spectroscopic methodologies into a single catheter system and/or into a single tissue identification system can be accomplished in any suitable manner. In some such embodiments, multiple spectroscopic methodologies can be combined in any desired manner utilizing the catheter system 200 and/or the tissue identification system 242 illustrated and described in relation to FIG. 2, e.g., by using a first spectroscopic methodology at a first time and then using a second spectroscopic methodology at a second time. Alternatively, in other such embodiments, multiple spectroscopic methodologies can be utilized substantially simultaneously. For example, FIG. 3 is a simplified schematic view of a portion of another embodiment of the catheter system 300 including another embodiment of the tissue identification system 342. More particularly, as illustrated in FIG. 3, two or more spectroscopic methodologies can be combined into one device by multiplexing the optical signal and sensing location into one or more light guides 322A at the treatment site 106.

The design of the catheter system 300 is substantially similar to the embodiments illustrated and described herein above. It is appreciated that various components of the catheter system 300, such as are shown in FIG. 1, are not illustrated in FIG. 3 for purposes of clarity and ease of illustration. However, it is appreciated that the catheter system 300 will likely include most, if not all, of such components. As shown in FIG. 3, the catheter system 300 again at least includes an energy source 324, e.g., a light source or other suitable energy source, and one or more energy guides 322A, e.g., light guides or other suitable energy guides. As above, the energy guides 322A are configured to guide energy from the energy source 324 into the balloon interior 146 (illustrated in FIG. 1) to generate plasma within the balloon fluid 132 (illustrated in FIG. 1) at or near a guide distal end 322D of the energy guide 322A disposed within the balloon interior 146 of the balloon 104 (illustrated in FIG. 1), which can be located at a treatment site 106 including a vessel wall 308A of a blood vessel 108 or a heart valve. Further, as above, the plasma formation can initiate a pressure wave and can initiate the rapid formation of one or more bubbles that can rapidly expand to a maximum size and then dissipate through a cavitation event that can launch a pressure wave upon collapse. The rapid expansion of the plasma-induced bubbles can generate one or more pressure waves within the balloon fluid 132 retained within the balloon 104 and thereby impart pressure waves upon the treatment site 106.

In the embodiment illustrated in FIG. 3, the tissue identification system 342 is configured to utilize two or more spectroscopic tissue identification methodologies to identify the type, size, quantity and location of any tissue at or near the treatment site 106 in order to optimize treatment in real-time. More specifically, as shown, the tissue identification system 342 can incorporate two tissue identification system members, e.g., a first tissue identification system member 342A and a second tissue identification system member 342B, which are each substantially similar in design and function to the tissue identification system 242 illustrated and described herein above in relation to FIG. 2. For example, each of the tissue identification members 342A, 342B can include one or more of a spectroscopic light source 360, a filter assembly 362, a beamsplitter 364, an optical element 366, a modulator 368, a light detector 370 and control electronics 372. Additionally, the tissue identification system members 342A, 342B can further include one or more light guides 322A, which can be the same light guides 322A that are used to direct the energy from the energy source 324, or can be dedicated light guides 322A that are used only for purposes of tissue identification. Each of the spectroscopic light source 360, the filter assembly 362, the beamsplitter 364, the optical element 366, the modulator 368, the light detector 370 and the control electronics 372 are substantially similar in design and function to what has been illustrated and described herein above in relation to FIG. 2. Accordingly, such components will not be described in detail herein again in relation to FIG. 3.

As shown in FIG. 3, the modulator 368 can be configured to couple the spectroscopic source beam 360A from the spectroscopic light sources 360 of each of the tissue identification system members 342A, 342B into the guide proximal end of a different light guide 322A, which then guides the respective spectroscopic source beam 360A into the balloon interior 146. After the spectroscopic source beam 360A from each of the spectroscopic light sources 360 is directed as desired toward the tissue of interest, at least a portion of the spectroscopic source beam 360A will be returned, e.g., reflected, refracted, scattered, phase changed, fluoresced, etc., by the tissue based on the properties of the tissue and be directed back toward the guide distal end 322D of the light guide 322A as respective returning identification beams 360B.

The respective returning identification beams 360B are then guided back through the light guide 322A from the guide distal end 322D to the guide proximal end before being directed back toward and through the modulator 368. Ultimately, as above, the desired portion of the respective returning identification beams 360B, which is selected based on the particular spectroscopic methodology being utilized at any given time, is directed to the respective light detector 370. The light detector 370 of each tissue identification system member 342A, 342B then captures and quantifies the characteristics of the respective returning identification beam 360B that has returned from the tissue of interest, and then generates an appropriate signal based on the detected characteristics and measured wavelength intensity of the respective returning identification beams 360B which is then sent to the control electronics 372 of the respective tissue identification system member 342A, 342B.

The control electronics 372 then analyzes the signal from the light detector 370 to provide an effective determination regarding the type, size, quantity and location of any tissue at or near the treatment site 106 in order to optimize treatment in real-time. More specifically, the control electronics 372 utilize an appropriate algorithm to effectively identify tissue type, size and location.

Moreover, it is appreciated that by utilizing multiple spectroscopic methodologies, a more robust tissue identification system 342 can be created to more effectively and accurately identify the type, size, quantity and location of any tissue at or near the treatment site 106 in order to optimize treatment in real-time.

Figure 4:
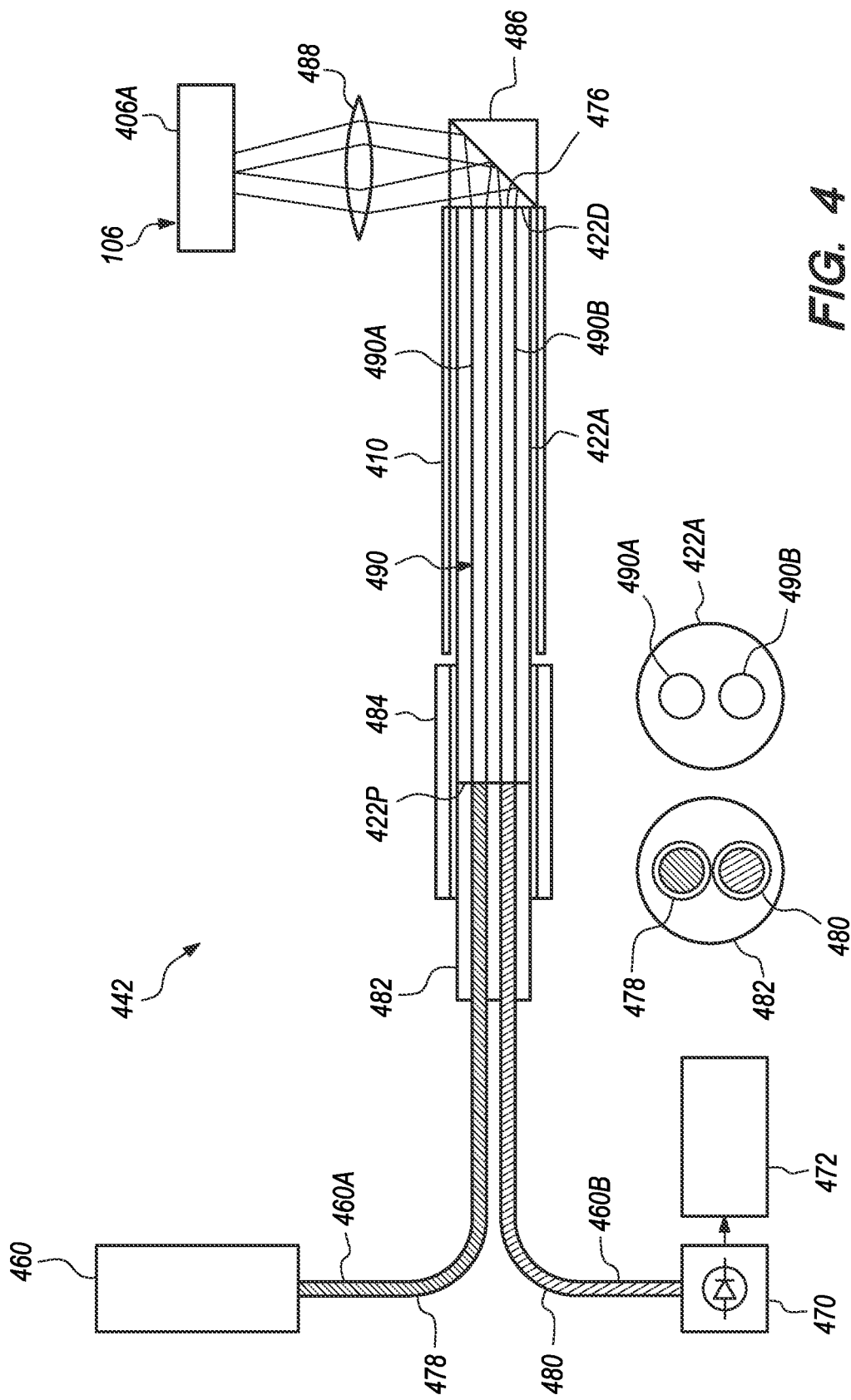
FIG. 4 is a simplified schematic view of a portion of still another embodiment of the tissue identification system.

FIG. 4 is a simplified schematic view of a portion of still another embodiment of the tissue identification system 442. In this embodiment, the tissue identification system 442 is somewhat different than in the previous embodiments. As illustrated, in this embodiment, the tissue identification system 442 includes one or more of a spectroscopic light source 460, an input fiber 478, an output fiber 480, a fiber housing 482, a light guide 422A, a coupling sleeve 484, a redirector 486, an optical element 488, e.g., a coupling lens, a light detector 470, and control electronics 472. FIG. 4 also shows a portion of the catheter shaft 410. Alternatively, the tissue identification system 442 can include more components or fewer components than those specifically illustrated in FIG. 4.

As with the previous embodiments, the spectroscopic light source 460 is configured to provide electromagnetic energy in the form of a spectroscopic source beam 460A that is used to diagnostically interrogate the tissue of interest, e.g., within a vascular lesion 406A at a treatment site 106. As shown, the spectroscopic source beam 460A is coupled into the input fiber 478 that is secured, at least in part, within the fiber housing 482. Additionally, as illustrated, the returning identification beam 460B is coupled into the output fiber 480 that is also secured, at least in part, within the fiber housing 482.

Further, as illustrated in this embodiment, the fiber housing 482, which holds at least a portion of both the input fiber 478 and the output fiber 480, is directly mechanically coupled to the light guide 422A, i.e. with the coupling sleeve 484. It is appreciated that the coupling sleeve 484 can have any suitable design for purposes of providing the direct mechanical coupling between the fiber housing 482 and the light guide 422A.

Additionally, as illustrated, the light guide 422A includes a plurality of guide cores 490, including at least a first guide core 490A and a second guide core 490B. During the coupling between the fiber housing 482 and the light guide 422A, the input fiber 478, and thus the spectroscopic source beam 460A retained therein, is coupled to the first guide core 490A of the light guide 422A, and the output fiber 482, and thus the returning identification beam 460B retained therein, is coupled to the second guide core 490B of the light guide 422A.

Thus, the spectroscopic source beam 460A is directed through the input fiber 478 and then through the first guide core 490A of the light guide 422A from the guide proximal end 422P to the guide distal end 422D. Additionally, as illustrated, the redirector 486, e.g., an RA prism or other suitable type of diverter, is positioned at or near the guide distal end 422D of the light guide 422A and is configured to more accurately and precisely direct the spectroscopic source beam 460A toward the tissue of interest, e.g., the vascular lesion 406A that is present at the treatment site 106. In certain embodiments, the tissue identification system 442 further includes the optical element 488, e.g., a focusing lens, to more accurately and precisely direct the spectroscopic source beam 460A toward the tissue of interest.

Additionally, as with the previous embodiments, depending upon the particular spectroscopic methodology being employed during any given use of the tissue identification system 442, at least a portion of the spectroscopic source beam 460A is returned, e.g., reflected, refracted, scattered, phase changed, fluoresced, etc., by the tissue based on the properties of the tissue and is directed back toward the guide distal end 422D of the light guide 422A as the returning identification beam 460B. More specifically, with the returning identification beam 460B being directed back through the optical element 488 and the redirector 486, the returning identification beam 460B is directed into the second guide core 490B at the guide distal end 422D of the light guide 422A via a distal light receiver 476 that is coupled to the guide distal end 422D of the light guide 422A adjacent to the second guide core 490B.

The returning identification beam 460B is then guided through the second guide core 490B from the guide distal end 422D to the guide proximal end 422P before being directed into the output fiber 480 that is directly mechanically coupled to the second guide core 490B. The returning identification beam 460B is then transmitted through the output fiber 480 to the light detector 470.

The light detector 470 then captures and quantifies the characteristics of the returning identification beam 460B that has returned from the tissue of interest, and then generates an appropriate signal based on the detected characteristics and measured wavelength intensity of the returning identification beam 460B which is then sent to the control electronics 472.

The control electronics 472 then analyzes the signal from the light detector 470 to provide an effective determination regarding the type, size, quantity and location of any tissue at or near the treatment site 106 in order to optimize treatment in real-time. More specifically, the control electronics 472 utilize an appropriate algorithm to effectively identify tissue type, size and location.

FIG. 4 also illustrates simplified cutaway views of the fiber housing 482 and the light guide 422A. More particularly, FIG. 4 illustrates a cutaway view of the fiber housing 482 which shows the input fiber 478 and the output fiber 480 being retained spaced apart from one another therein. Similarly, FIG. 4 also illustrates a cutaway view of the light guide 422A which shows the first guide core 490A and the second guide core 490B being positioned spaced apart from one another therein.

It is appreciated that the unique design of the tissue identification system 442 as illustrated in FIG. 4 provides a somewhat simplified overall tissue identification system 442, by enabling much of the optics present at the proximal end in previous embodiments to be eliminated.

Figure 5:
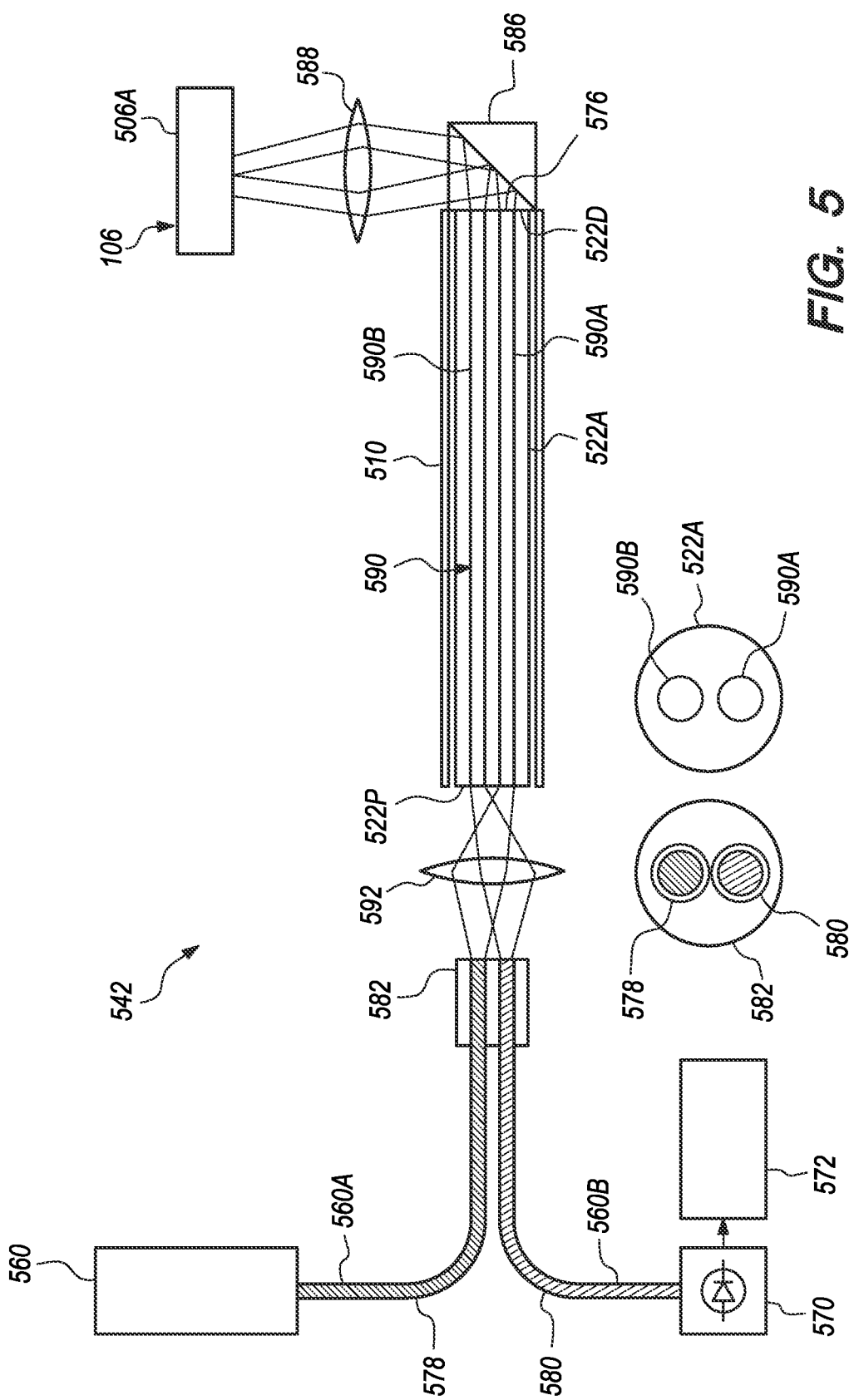
FIG. 5 is a simplified schematic view of a portion of yet another embodiment of the tissue identification system.

FIG. 5 is a simplified schematic view of a portion of yet another embodiment of the tissue identification system 542. As illustrated, the tissue identification system 542 is substantially similar to the embodiment that was illustrated and described in relation to FIG. 4. For example, as shown, the tissue identification system 542 again includes one or more of a spectroscopic light source 560, an input fiber 578, an output fiber 580, a fiber housing 582, a light guide 522A, a redirector 586, an optical element 588, e.g., a coupling lens, a light detector 570, and control electronics 572. FIG. 5 also shows a portion of the catheter shaft 510. However, in this embodiment, the coupling sleeve 484 has been replaced with coupling optics 592.

As with the previous embodiments, the spectroscopic light source 560 is configured to provide electromagnetic energy in the form of a spectroscopic source beam 560A that is used to diagnostically interrogate the tissue of interest, e.g., within a vascular lesion 506A at a treatment site 106. As shown, the spectroscopic source beam 560A is coupled into the input fiber 578 that is secured, at least in part, within the fiber housing 582. Additionally, as illustrated, the returning identification beam 560B is coupled into the output fiber 580 that is also secured, at least in part, within the fiber housing 582.

Additionally, as illustrated, the light guide 522A again includes a plurality of guide cores 590, including at least a first guide core 590A and a second guide core 590B.

In this embodiment, the coupling optics 592 are utilized to provide the desired optical coupling between the spectroscopic source beam 560A as it emerges from the input fiber 578 and the first guide core 590A of the light guide 522A, as well as the desired optical coupling between the returning identification beam 560B as it emerges from the second guide core 590B of the light guide 522A and the output fiber 580.

Thus, the spectroscopic source beam 560A is directed through the input fiber 578 and then through the first guide core 590A of the light guide 522A from the guide proximal end 522P to the guide distal end 522D. Additionally, as illustrated, the redirector 586, e.g., an RA prism or other suitable type of diverter, is positioned at or near the guide distal end 522D of the light guide 522A and is configured to more accurately and precisely direct the spectroscopic source beam 560A toward the tissue of interest, e.g., the vascular lesion 506A that is present at the treatment site 106. In certain embodiments, the tissue identification system 542 further includes the optical element 588, e.g., a focusing lens, to more accurately and precisely direct the spectroscopic source beam 560A toward the tissue of interest.

Additionally, as with the previous embodiments, depending upon the particular spectroscopic methodology being employed during any given use of the tissue identification system 542, at least a portion of the spectroscopic source beam 560A is returned, e.g., reflected, refracted, scattered, phase changed, fluoresced, etc., by the tissue based on the properties of the tissue and is directed back toward the guide distal end 522D of the light guide 522A as the returning identification beam 560B. More specifically, with the returning identification beam 560B being directed back through the optical element 588 and the redirector 586, the returning identification beam 560B is directed into the second guide core 590B at the guide distal end 522D of the light guide 522A via a distal light receiver 576 that is coupled to the guide distal end 522D of the light guide 522A adjacent to the second guide core 590B.

The returning identification beam 560B is then guided through the second guide core 590B from the guide distal end 522D to the guide proximal end 522P before being directed into the output fiber 580 that is optically coupled to the second guide core 590B. The returning identification beam 560B is then transmitted through the output fiber 580 to the light detector 570.

The light detector 570 then captures and quantifies the characteristics of the returning identification beam 560B that has returned from the tissue of interest, and then generates an appropriate signal based on the detected characteristics and measured wavelength intensity of the returning identification beam 560B which is then sent to the control electronics 572.

The control electronics 572 then analyzes the signal from the light detector 570 to provide an effective determination regarding the type, size, quantity and location of any tissue at or near the treatment site 106 in order to optimize treatment in real-time. More specifically, the control electronics 572 utilize an appropriate algorithm to effectively identify tissue type, size and location.

Similar to the previous embodiment, FIG. 5 also illustrates simplified cutaway views of the fiber housing 582, with the input fiber 578 and the output fiber 580 being retained spaced apart from one another therein, and the light guide 522A, with the first guide core 590A and the second guide core 590B being positioned spaced apart from one another therein.

It should be noted that, as used in this specification and the appended claims, the singular forms "a," "an," and "the" include plural referents unless the content and/or context clearly dictates otherwise. It should also be noted that the term "or" is generally employed in its sense including "and/or" unless the content or context clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

The headings used herein are provided for consistency with suggestions under 37 CFR 1.77 or otherwise to provide organizational cues. These headings shall not be viewed to limit or characterize the invention(s) set out in any claims that may issue from this disclosure. As an example, a description of a technology in the "Background" is not an admission that technology is prior art to any invention(s) in this disclosure. Neither is the "Summary" or "Abstract" to be considered as a characterization of the invention(s) set forth in issued claims.

The embodiments described herein are not intended to be exhaustive or to limit the invention to the precise forms disclosed in the present detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

It is understood that although a number of different embodiments of the catheter system and the tissue identification system have been illustrated and described herein, one or more features of any one embodiment can be combined with one or more features of one or more of the other embodiments, provided that such combination satisfies the intent of the present invention.

While a number of exemplary aspects and embodiments of the catheter system and the tissue identification system have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope, and no limitations are intended to the details of construction or design herein shown.

What is claimed is:

1. A catheter system for treating a vascular lesion within or adjacent to a vessel wall, the catheter system comprising:
   an energy source that generates energy;
   a balloon that is positionable substantially adjacent to the vascular lesion, the balloon having a balloon wall that defines a balloon interior, the balloon being configured to retain a balloon fluid within the balloon interior;
   an energy guide that is configured to receive energy from the energy source and guide the energy into the balloon interior, the energy from the energy source being emitted at a guide distal end of the energy guide to energize a plasma generator so that plasma is generated in the balloon fluid within the balloon interior, the plasma generation causing rapid bubble formation and imparting pressure waves upon the balloon wall substantially adjacent to the vascular lesion; and
   a tissue identification system that is configured to spectroscopically analyze tissue within the vascular lesion, the tissue identification system using the energy guide to direct energy from the energy source toward the vascular lesion.

2. The catheter system of claim 1 wherein the tissue identification system is configured to utilize spectroscopic tissue identification to provide real-time feedback regarding tissue type and quantity within the vascular lesion.

3. The catheter system of claim 1 wherein the energy source generates pulses of energy that are guided along the energy guide into the balloon interior to induce the plasma formation in the balloon fluid within the balloon interior.

4. The catheter system of claim 1 wherein the energy source is a laser source that provides pulses of laser energy, and the energy guide includes an optical fiber.

5. The catheter system of claim 1 wherein the energy source is a high voltage energy source that provides pulses of high voltage.

6. The catheter system of claim 1 wherein the energy guide includes an electrode pair including spaced apart electrodes that extend into the balloon interior; and wherein pulses of high voltage from the energy source are applied to the electrodes and form an electrical arc across the electrodes.

7. The catheter system of claim 1 wherein the tissue identification system includes a spectroscopic light source that is configured to provide electromagnetic energy in the form of a spectroscopic source beam that is used to diagnostically interrogate the tissue within the vascular lesion.

8. The catheter system of claim 7 wherein the spectroscopic light source is a broadband light source with a targeted wavelength range that is based at least in part on optical characteristics of the tissue being analyzed.

9. The catheter system of claim 7 wherein the spectroscopic light source is a coherent, monochromatic light source with a targeted wavelength that is based at least in part on optical characteristics of the tissue being analyzed.

10. The catheter system of claim 7 wherein the tissue identification system includes a light guide that receives the spectroscopic source beam and guides the spectroscopic source beam from a guide proximal end to a guide distal end that is positioned within the balloon interior.

11. The catheter system of claim 10 wherein the tissue identification system further includes a modulator that optically couples the spectroscopic source beam into the light guide.

12. The catheter system of claim 11 wherein the modulator further couples the energy from the energy source into the energy guide.

13. The catheter system of claim 10 wherein the spectroscopic source beam is retained within an input fiber that is coupled to the spectroscopic light source.

14. The catheter system of claim 13 wherein the input fiber is directly mechanically coupled to the light guide so that the spectroscopic source beam is optically coupled into the light guide.

15. The catheter system of claim 13 wherein the tissue identification system further includes coupling optics so that the spectroscopic source beam is optically coupled into the light guide.

16. The catheter system of claim 13 wherein the light guide includes a plurality of guide cores; and wherein the spectroscopic source beam is optically coupled into a first guide core of the plurality of guide cores.

17. The catheter system of claim 10 wherein the light guide directs the spectroscopic source beam toward the vascular lesion.

18. The catheter system of claim 17 wherein the light guide includes a diverter that is coupled to the guide distal end to direct the spectroscopic source beam toward the vascular lesion.

19. The catheter system of claim 7 wherein at least a portion of the spectroscopic source beam is returned by the tissue being analyzed as a returning identification beam that is directed back toward the guide distal end of the light guide.

20. The catheter system of claim 19 wherein the returning identification beam is guided by the light guide from the guide distal end to the guide proximal end, and is then directed toward a light detector that is configured to capture and quantify detected characteristics of the returning identification beam.

21. The catheter system of claim 20 wherein the modulator directs the returning identification beam toward the light detector, and wherein the returning identification beam is retained within an output fiber that is coupled to the light detector.

22. The catheter system of claim 21 wherein the output fiber is directly mechanically coupled to the light guide so that the returning identification beam is optically coupled from the light guide into the output fiber.

23. The catheter system of claim 21 wherein the tissue identification system further includes coupling optics so that the returning identification beam is optically coupled from the light guide into the output fiber.

24. The catheter system of claim 20 wherein the light detector generates a signal based on the detected characteristics of the returning identification beam and sends the signal to control electronics.

25. The catheter system of claim 24 wherein the control electronics analyze the signal to determine the tissue type and quantity within the vascular lesion.

26. The catheter system of claim 1 wherein the tissue identification system utilizes at least one of specular reflectance spectroscopy, diffuse reflectance spectroscopy, fluorescence spectroscopy and Raman spectroscopy.

27. The catheter system of claim 1 wherein the tissue identification system utilizes at least two of specular reflectance spectroscopy, diffuse reflectance spectroscopy, fluorescence spectroscopy and Raman spectroscopy.

28. A method for treating a vascular lesion within or adjacent to a vessel wall, the method comprising the steps of:
positioning a balloon substantially adjacent to the vascular lesion, the balloon having a balloon wall that defines a balloon interior;
retaining a balloon fluid within the balloon interior;
generating energy with an energy source so that the energy from the energy source is received with an energy guide;
guiding the energy into the balloon interior with the energy guide, the energy from the energy source being emitted at a guide distal end of the energy guide to energize a plasma generator so that a plasma is formed generated in the balloon fluid within the balloon interior, the plasma generation causing rapid bubble formation and imparting pressure waves upon the balloon wall substantially adjacent to the vascular lesion; and
spectroscopically analyzing tissue within the vascular lesion with a tissue identification system, the tissue identification system using the energy guide to direct energy from the energy source toward the vascular lesion.

29. The catheter system of claim 1 wherein the balloon includes a drug-eluting coating.

30. The method of claim 28 wherein the step of generating energy includes the energy source being a laser source that provides pulses of laser energy; and wherein the step of guiding the energy includes the energy guide including an optical fiber.

31. The method of claim 28 wherein the step of spectroscopically analyzing includes providing electromagnetic energy from a spectroscopic light source in the form of a spectroscopic source beam, and diagnostically interrogating the tissue within the vascular lesion with the spectroscopic source beam.

* * * * *